US011457879B2

(12) United States Patent
Chen et al.

(10) Patent No.: US 11,457,879 B2
(45) Date of Patent: *Oct. 4, 2022

(54) COLLIMATOR OF A SCANNING SYSTEM

(71) Applicant: SHANGHAI UNITED IMAGING HEALTHCARE CO., LTD., Shanghai (CN)

(72) Inventors: Guanghui Chen, Shanghai (CN); Tian Xu, Shanghai (CN); Huaifang Jiang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 33 days.

This patent is subject to a terminal disclaimer.

(21) Appl. No.: 17/067,936

(22) Filed: Oct. 12, 2020

(65) Prior Publication Data

US 2021/0085263 A1 Mar. 25, 2021

Related U.S. Application Data

(63) Continuation of application No. 15/772,068, filed as application No. PCT/CN2016/103800 on Oct. 28, 2016, now Pat. No. 10,799,190.

(30) Foreign Application Priority Data

| Oct. 30, 2015 | (CN) | 201520858351.6 |
| Dec. 25, 2015 | (CN) | 201521103625.7 |
| Dec. 25, 2015 | (CN) | 201521103639.9 |

(51) Int. Cl.
*A61B 6/06* (2006.01)
*A61B 6/03* (2006.01)
(Continued)

(52) U.S. Cl.
CPC .............. *A61B 6/032* (2013.01); *A61B 6/027* (2013.01); *A61B 6/06* (2013.01); *G21K 1/04* (2013.01)

(58) Field of Classification Search
CPC ........... G21K 1/04; G21K 1/02; G21K 1/025; G21K 1/046; A61B 6/00; A61B 6/03;
(Continued)

(56) References Cited

U.S. PATENT DOCUMENTS

| 5,054,041 A | 10/1991 | Hampel |
| 5,160,847 A | 11/1992 | Leavitt et al. |

(Continued)

FOREIGN PATENT DOCUMENTS

| CN | 102467985 A | 5/2012 |
| CN | 203016974 U | 6/2013 |

(Continued)

OTHER PUBLICATIONS

International Search Report in PCT/CN2016/103800 dated Jan. 23, 2017, 8 pages.

(Continued)

*Primary Examiner* — Jurie Yun
(74) *Attorney, Agent, or Firm* — Metis IP LLC

(57) ABSTRACT

The present disclosure provides a collimator. The collimator includes a slice module, a filter module, and a support and protection module. The slice module and the filter module are detachably connected with the support and protection module. The rays strike on the collimator and pass through the slice module and the filter module in order. The slice module is configured to adjust the fan-beam width of the rays striking on the collimator. The filter module is configured to make the rays pass through different filters to implement different types of scanning.

20 Claims, 19 Drawing Sheets

(51) Int. Cl.
    *G21K 1/04*     (2006.01)
    *A61B 6/02*     (2006.01)

(58) Field of Classification Search
    CPC .. A61B 6/02; A61B 6/06; A61B 6/032; A61B 6/027
    See application file for complete search history.

(56) References Cited

U.S. PATENT DOCUMENTS

| | | |
|---|---|---|
| 10,799,190 B2 * | 10/2020 | Chen ................ A61B 6/06 |
| 2010/0119033 A1 | 5/2010 | Li et al. |
| 2011/0249787 A1 | 10/2011 | Frey et al. |
| 2018/0168524 A1 | 6/2018 | Melman |
| 2018/0310901 A1 | 11/2018 | Garlow et al. |

FOREIGN PATENT DOCUMENTS

| | | |
|---|---|---|
| CN | 103271747 A | 9/2013 |
| CN | 205181365 U | 4/2016 |
| CN | 205433722 U | 8/2016 |
| CN | 205514648 U | 8/2016 |

OTHER PUBLICATIONS

Written Opinion in PCT/CN2016/103800 dated Jan. 23, 2017, 14 pages.
The Extended European Search Report in European Application No. 16859086.7 dated Jun. 6, 2019, 7 pages.

\* cited by examiner

COLLIMATOR OF A SCANNING SYSTEM

CROSS-REFERENCE TO RELATED APPLICATIONS

This application is a continuation application of U.S. patent application Ser. No. 15/772,068, filed on Apr. 29, 2018, which is a U.S. national stage application under 35 U.S.C. § 371 of International Application No. PCT/CN2016/103800, filed on Oct. 28, 2016, designating the United States of America, which claims priority of Chinese Application Nos. 201520858351.6 filed on Oct. 30, 2015, 201521103639.9 filed on Dec. 25, 2015, and 201521103625.7 filed on Dec. 25, 2015, the entire contents of each of which are hereby incorporated by reference.

TECHNICAL FIELD

This application generally relates to a scanning apparatus, and more particularly, relates to a collimator in a Computed Tomography (CT) scanning system.

BACKGROUND

X-ray Computed Tomography (X-ray CT) is a technique of reconstructing medical images based on digital geometry processing. The technology is implemented by radiating a human body using X-rays around a single axis of rotation. Because different tissues in the human body may have different absorption coefficients (or referred to as radiodensity) of X-rays, cross-sectional images can be reconstructed based on three-dimensional (3D) technology implemented by a computer.

A CT scanning system generally includes an X-ray radiation device, a detector, and a gantry. A collimator is an important component in the CT scanning system. The collimator is generally placed in the gantry and located between the X-ray radiation device and a patient to block part of X-rays. The collimator may include one or more openings. The region of radiation may be adjusted through adjusting the size(s) of the one or more openings to keep the patient from receiving unnecessary X-rays radiation and to reduce the radiation dose. The collimator may also control the thickness of slices to be scanned to meet an imaging condition. The reasonableness of the structure of the collimator directly affects the imaging quality in the CT scanning system. The existing collimator usually has a complex structure and is not easy to disassemble, which brings inconvenience to regular maintenance. In view of the above problems, the present disclosure provides a feasible optimization design for the structure of the collimator.

SUMMARY

The collimator provided in the present disclosure includes optimized and changed functional components of collimators in the existing technology, which allows the function of protection by blocking radiation, the function of filtering, the function of adjusting the width of a ray beam to be realized by independent components. There is no interference among the independent components or structural crossover when the independent components are put together, which reduces the complexity of the collimator system. Meanwhile, the replacement of a module may be achieved by simple disassembly, and so it is convenient to for an engineer to perform regular maintenance.

The present disclosure provides a collimator. The collimator may include a slice module, a filter module, and a support and protection module. The slice module and the filter module may be detachably connected with the support and protection module. Rays may strike on the collimator and pass through the slice module and the filter module in order. The slice module may adjust the fan-beam width of the rays striking on the collimator. The filter module may be configured to allow the rays to pass through different filters to implement different types of scanning.

The present disclosure provides a collimator. The collimator may include a slice module, an actuator, and a support. The slice module may include two slice plates. The two slice plates and the actuator after being assembled may be placed on the support. An opening may be formed between the two slice plates. The actuator may be configured to control movement of the two slice plates to change the size of the opening.

In some embodiments, the support may include a plate with a hollow part. The hollow part of the support may be positioned corresponding to the opening.

In some embodiments, the slice module may include a drum that may rotate around an axis thereof. A lateral surface of the drum may have a through hole to allow rays to pass through.

In some embodiments, the collimator may further include a slice plate with an opening. The slice plate may be placed on an external side of the drum. The rays may pass through the opening and the through hole, and exit from a side of the drum opposite to the opening.

In some embodiments, the opening may have the shape of a stripe, a rectangle, or an oval.

In some embodiments, the slice plate may be a flat plate and the through hole may extend in a direction perpendicular to the plane formed by the slice plate.

In some embodiments, the slice module may include multiple slice plates with openings and a drum. The drum may include multiple through holes, and positions of the multiple through holes may not overlap with each other.

In some embodiments, the drum may be a polygonal cylinder. The lateral surface of the drum may include multiple faces forming pairs each of which are opposite to each other. Two opposite faces of the multiple faces may form a face pair. The count of the through holes, the count of slice plates, and the count of the face pairs may be the same. Each slice plate of the multiple slice plates may be mounted on one face of each face pair. Each through hole may connect two faces of each face pair.

In some embodiments, the filter module may include a filter replacing unit and a filter floating base. The filter replacing unit may be detachably mounted on the filter floating base.

In some embodiments, the filter replacing unit may include a filter holder, a filter mounting plate, and one or more first filters. The one or more first filters may be mounted on the filter holder via the filter mounting plate. The filter replacing unit may be detachably mounted on the filter floating base.

In some embodiments, the filter floating base may include an optical guide shaft, a linear bearing, a base, and one or more second filters. The linear bearing and the one or more second filters may be placed on the base. The optical guide shaft may be located within the linear bearing. The optical guide shaft may rotate and drive the base to move along an axial direction of the optical guide shaft.

In some embodiments, the count of the one or more first filters may be the same as the count of the one or more second filters. The one or more first filters and the one or more second filters may be of the same type. The one or more first filters and the one or more second filters may be arranged in one-to-one correspondence.

In some embodiments, the one or more first filters and the one or more second filters may be butterfly filters or plate filters.

In some embodiments, the one or more first filters and the one or more second filters may be arranged along the axial direction of the optical guide shaft.

In some embodiments, the support and protection module may have a box structure. The box structure may have a top opening and a side opening. The filter module may be placed in the box structure from the side opening, and the slice module may be placed in the box structure from the top opening.

BRIEF DESCRIPTION OF THE DRAWINGS

In order to illustrate the technical solutions related to the embodiments of the present disclosure, a brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, like reference numerals in the drawings refer to like structures and operations.

DETAILED DESCRIPTION

As used in the present disclosure, the singular forms "a," "an," and/or "the" may be intended to include the plural forms as well, unless the context clearly indicates otherwise. The terms "include" and/or "comprise," when used in this disclosure, specify the presence of operations and/or elements, but do not exclude the presence or addition of one or more other operations and/or elements in method and/or system. The term "base on" specifies "base on at least partially." The term "an embodiment" specifies "at least one embodiment." A definition of other terms will be provided in the description below.

A flowchart is used in the present disclosure to describe operations performed by a system in accordance with some embodiments of the present disclosure. It should be understood that preceding or following operations are not necessarily performed exactly in sequence. Instead, various operations may be performed in reverse sequence and/or simultaneously. Moreover, other operations may also be added into these procedures, or one or more operations may be removed from these procedures.

The present disclosure generally relates to a scanning system and, more specifically, to a medical scanning system. The medical scanning system may include a radiation device, a collimator, a detector, an examination table, and an image reconstruction system. The collimator may include a slice module, a filter module, a support and protection module, etc. In some embodiments, the slice module may include two slice plates, which may be set away by a distance to form an opening. In some embodiments, the slice module may include a drum. In some embodiments, the slice module may include one or more slice plates with openings and the one or more slice plates may be settled on the lateral surface of the drum.

Figure 1:
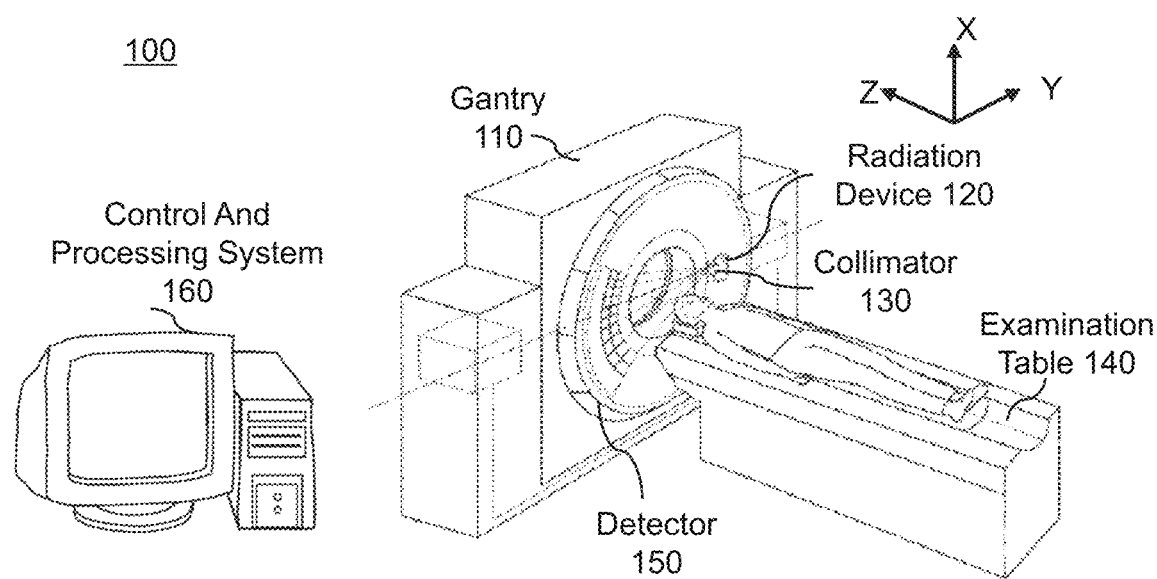
FIG. 1 illustrates an exemplary scanning system according to some embodiments of the present disclosure.

FIG. 1 illustrates an exemplary scanning system according to some embodiments of the present disclosure. The scanning system 100 may include a gantry 110, a radiation device 120, a collimator 130, an examination table 140, a detector 150, and a control and processing system 160. The gantry 110 may support one or more components in the scanning system 100. In some embodiments, the gantry 110 may include a scanning bore. In some embodiments, the scanning bore may be round. The radiation device 120 may radiate rays or signals. The rays may include X-rays, y-rays, etc. The collimator 130 may collimate the rays by adjusting the width and direction of fan-beam of the rays. A detection object may be placed on the examination table 140. The detection object may be a person or a subject. The detector 150 may receive the rays that have passed through the detection object. The detector 150 may be disposed opposite to the radiation device 120 in the gantry 110. The control and processing system 160 may control the radiation device 120, the collimator 130, and the examination table 140 (e.g., locations and working statuses of the components). Further, the control and processing system 160 may generate and display a medical image.

In some embodiments, during a detection, a patient on the examination table 140 may be pushed along the Z-axis direction into the scanning bore. The Z-axis direction may be the direction that the examination table 140 moves along. Further, the radiation device 120 may rotate around the Z-axis direction and emit X-rays. The detector 150 may be settled opposite to the radiation device 120 and may rotate with the radiation device 120 synchronously. During the rotation, the detector 150 may collect scanning data. The scanning data may be data of X-rays passing through the body of the patient. After the detection, the detector 150 may transmit the acquired scanning data to the control and processing system 160. Further, the control and processing system 160 may reconstruct a medical image of the patient based on the acquired scanning data.

In some embodiments, the scanning system 100 may perform spiral scan. For example, during a scan, the patient may move along the Z-axis direction in the scanning bore. Meanwhile, the radiation device 120 may rotate around the Z-axis direction. Thus, relative to the patient, the radiation device 120 may form a spiral trajectory. In some embodiments, the detector 150 may transmit the acquired data from the spiral scan to the control and processing system 160. The control and processing system 160 may reconstruct a medical image with a larger width in the Z-axis direction.

Figure 2:
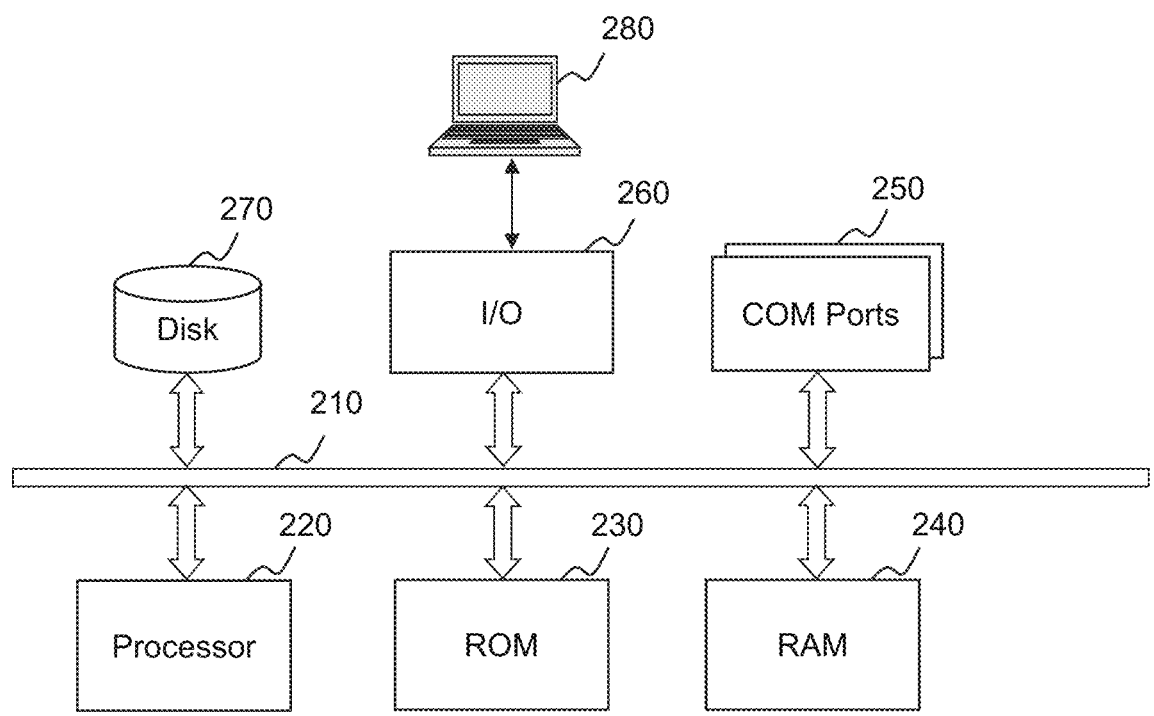
FIG. 2 is a configuration diagram of an exemplary control and processing system according to some embodiments of the present disclosure.

FIG. 2 is a configuration diagram of an exemplary control and processing system according to some embodiments of the present disclosure. As shown in FIG. 2, the control and processing system 160 may include a bus 210, a processor 220, a Read Only Memory (ROM) 230, a Radom Access Memory (RAM) 240, a communication port 250, an input/output port 260, a hard disk 270, and a display 280 connected with the input/output port 260. The connection between any two of the components of the control and processing system 160 may be wired, wireless, or a combination thereof. Any of the components of the control and processing sub-system 160 may be local, remote, or a combination thereof. The data bus 210 may be configured to transmit data information. In some embodiments, hardware components within the control and processing system 160 may transmit data through the data bus 210. For example, the processor 220 may transmit data to the input/output port 260, or other component in the control and processing system 160. It should be noted that the data may be real data, instruction codes, status information, or control information. In some embodiments, the bus 210 may be an Industry Standard Architecture (ISA) bus, an Extended Industry Standard Architecture (EISA) bus, a Video Electronics Standards Association (VESA) bus, a Peripheral Component Interconnect (PCI) bus, etc. The processor 220 may run logical operations, process data, and generate instructions. In some embodiments, the processor 220 may obtain data or instructions from internal storage. The internal storage may include a ROM, a RAM, a Cache (not shown in FIG. 2), etc. In some embodiments, the processor 220 may include multiple sub-processors. The sub-processors may implement multiple functions of the control and processing system 160. The ROM 230 may perform Power On Self Test (POST), initialize components in the control and processing system 160, drive input/output of the control and processing system 160, etc. In some embodiments, the ROM 230 may include a Programmable Read-Only Memory (PROM), an Electrically Programmable Read-Only-Memory (EPROM), an One Time Programming Read-Only Memory (OTPROM), etc. The RAM 240 may store an operation system, applications, data, etc. In some embodiments, the RAM 240 may include a Static Random Access Memory (SRAM), a Dynamic Random Access Memory (DRAM), etc. The communication port 250 may be connected with the system and an external network for communication between them. In some embodiments, the communication port 250 may include a File Transfer Protocol (FTP) port, a Hyper Text Transport Protocol (HTTP) port, a Domain Name Server (DNS) port, etc. The input/output port 260 may control and exchange information between an external device or circuit and the processor 220. In some embodiments, the input/output port 260 may include an Attention (AT) port, a Peripheral Component Interconnect (PCI) port, an Integrated Dive Electronics (IDE) port, etc. The hard disk 270 may store information/data produced by or received from the control and processing system 160 or information or data received from devices outside of the control and processing system 160. In some embodiments, the hard disk 270 may include a Hard Disk Drive (HDD), a Solid State Disk (SSD), or a Hybrid Hard Drive (HHD), etc. The display 280 may display information/data generated by the control and processing system 160 to users. The display 280 may include a physical display, e.g., a display with a loud speaker, a Liquid Crystal Display (LCD), a light-emitting diode (LED) display, an Organic Light Emitting Diode (OLED) display, an electronic ink display (E-Ink), etc.

Figure 3:
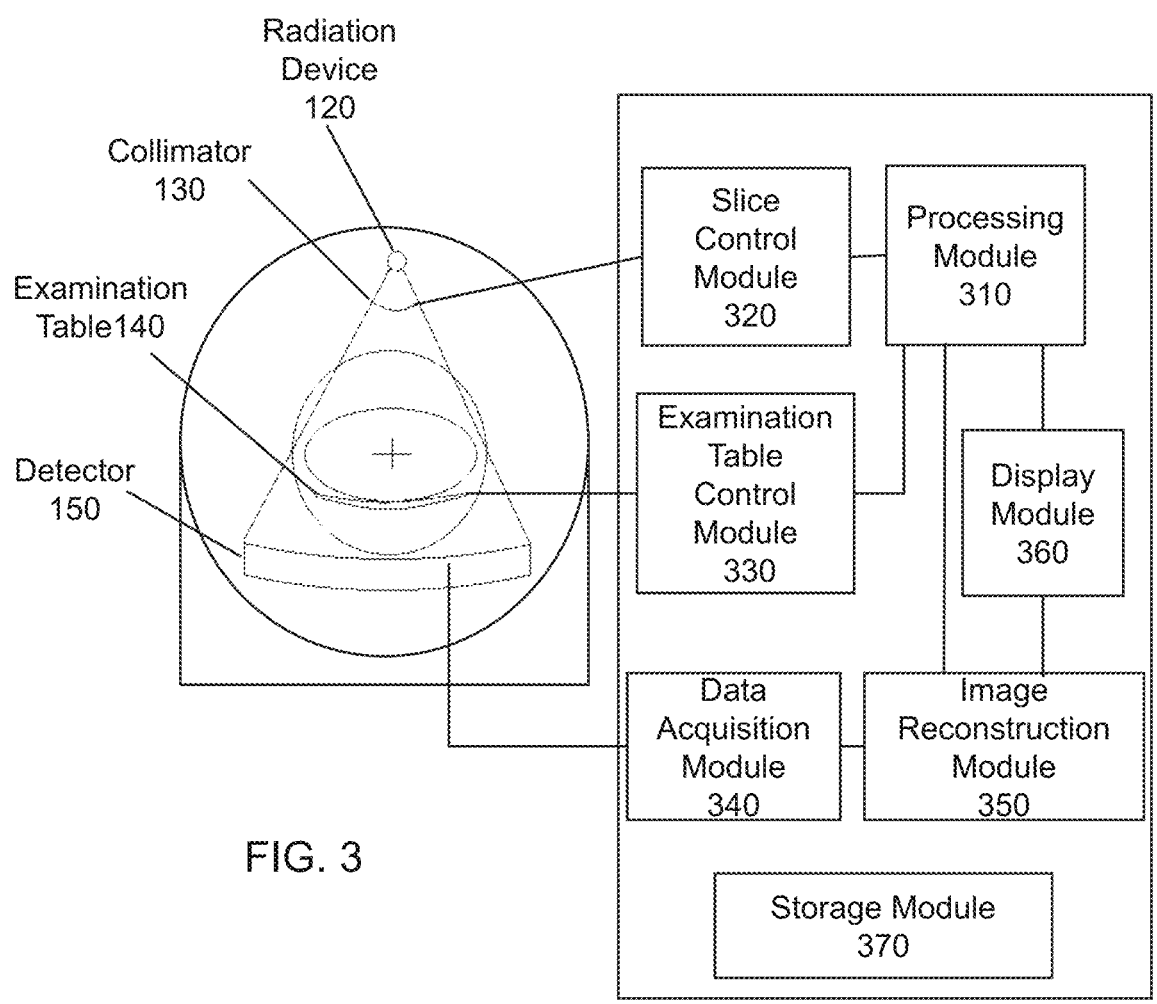
FIG. 3 is a block diagram of an exemplary control and processing system according to some embodiments of the present disclosure.

FIG. 3 is a block diagram of an exemplary control and processing system according to some embodiments of the present disclosure. The control and processing system 160 may include a processing module 310, a slice control module 320, an examination table control module 330, a data acquisition module 340, an image reconstruction module 350, a display module 360, and a storage module 370. The connection between any two the components of the control and processing system 160 may be wired, wireless, or a combination thereof. Any of the components of the control and processing system 160 may be local, remote, or a combination of thereof. The terms "module," "sub-module," "unit," and/or "sub-unit" described in the present disclosure specify logic or software instructions stored in hardware or firmware. The "module," "sub-module," "unit," "sub-unit" may be implemented by a software module or a hardware module or be stored in any computer readable non-transitory medium or other storage. In some embodiments, a software module may be compiled and connected with an executable program. Obviously, such a software module may respond to received information from itself or other modules and/or make a response once an event or interruption is detected. A software module executable by a computing device (e.g., the processor 220) to perform operations may be implemented on a computer readable medium. Such a computer readable medium may be an optical disc, a digital optical disc, a flash disc, a disk, or a medium of another type. Such a software module may be obtained by downloading digital data (the digital data downloaded may include data stored in a compressed package or an installation package; the data need to be extracted or decoded before being executed). The software codes may be partially or entirely stored in the storage of the computing device that is capable of executing corresponding operations of the codes. Software instructions may be encoded in firmware, e.g., an EPROM. Obviously, firmware may include connected logical units, e.g., a gate, a trigger, and/or a programmable unit (a programmable gate array or processor). The module or the computing device may be implemented as a software module preferably, or also may be implemented in hardware or firmware. Generally, such a module may be a logical module, and not limited by its specific physical form or storage. A module may be combined with another module, or segmented into multiple sub-modules.

The processing module 310 may perform numerical computations, perform logical processes, and generate instructions. The function of the processing module 310 may be achieved by the processor 220 in FIG. 2. In some embodiments, the processing module 310 may obtain data/information from the data acquisition module 340 or the storage module 370. Further, the processing module 310 may perform numerical computations or logical processes and transmit the processed data/information to the slice control module 320, the examination table control module 330, the display module 360, or the storage module 370. In some embodiments, the processing module 310 may perform numerical computations on external data obtained by the data acquisition module 340 to determine needed target parameters. For example, the processing module 310 may determine intensities of X-rays that have passed through a detection object at various times, angles, or locations to further determine absorption coefficient of X-rays of a corresponding part of the detection object. In some embodiments, the processing module 310 may perform logical judgment and make a decision on the obtained data/information to generate an executable instruction. For example, the processing module 310 may obtain information relating to a target location of the examination table 140 from the data acquisition module 340 and/or the storage module 370. Further, the processing module 310 may detect a current location of the examination table 140 and compare the current location with the target location. When the current location does not match the target location, the processing module 310 may generate an instruction for moving the examination table. The examination table control module 330 may cause the examination table 140 to move to the target location based on the instruction. When the examination table 140 arrives at the target location, the processing module 310 may generate an instruction for stopping the movement of the examination table. In some embodiments, the processing module 310 may generate an instruction for activating the radiation device 120. The radiation device 120 may be activated according to the activation instruction. The activation instruction of the radiation device 120 may include a preset opening time of the radiation device 120. Further, the processing module 310 may detect an opening time of the radiation device 120 and compare the opening time with the preset opening time. When the opening time of the radiation device 120 equals to the preset opening time, the processing module 310 may generate an instruction for shutting down the radiation device 120. The radiation device 120 may shut down according to the shutdown instruction. In some embodiments, the processing module 310 may receive data/information passively, or receive data/information actively by the data acquisition module 340 according to a request by a user or other modules.

The slice control module 320 may execute slice control instructions generated by the processing module 310 or inputted by a user. Functions of the slice control module may be achieved by the processor 220 in FIG. 2. The slice control instructions may include an instruction for adjusting the position of a slice (also referred to herein as a slice position adjusting instruction), an instruction for adjusting the opening size (also referred to herein as an opening size adjusting instruction), or an instruction for adjusting an angle (also referred to herein as an angle adjusting instruction). The slice position adjusting instruction may be used to adjust the position of the slice module. The opening size adjusting instruction may be used to adjust the opening size of an opening of the slice module. The angle adjusting instruction may be used to adjust the rotation angle of the slice module. In some embodiments, the slice control module 320 may receive a slice position adjusting instruction generated by the processing module 310 or inputted by a user. The slice position adjusting instruction may include information relating to one or more target positions. Further, the slice control module 320 may control the slice module 320 or one or more components of the slice module to move to corresponding target position(s). The slice control module 320 may receive an opening size adjusting instruction or an angle adjusting instruction generated by the processing module 310 or inputted by a user. The slice control module 320 may adjust the slice module or components in the slice module according to an opening size adjusting instruction.

The examination table control module 330 may execute an instruction for controlling the examination table (also referred to herein as an examination table control instruction) generated by the processing module 310 or inputted by a user. Functions of the examination table control module 330 may be achieved by the processor 220 in FIG. 2. The examination table control instruction may include an instruction for adjusting a position of the examination table 140 (also referred to herein as an examination table adjusting instruction) and an instruction for adjusting the moving speed of the examination table 140 (also referred to herein as an examination table speed adjusting instruction). The examination table position adjusting instruction may be used to adjust the position of the examination table 140 along the Z-axis direction. The examination table speed adjusting instruction may be used to adjust the moving speed of the examination table 140 during the movement of the examination table 140 along the Z-axis direction. In some embodiments, the examination table position adjusting instruction may include information relating to a target position of the examination table 140. The examination table speed adjusting instruction may include information relating to a preset moving speed of the examination table 140. In some embodiments, the examination table control module 330 may receive an examination table position adjusting instruction generated by the processing module 310 or inputted by a user. The examination table control module 330 may control the examination table 140 to move to the target position along the Z-axis direction based on the information relating to the target position of the examination table position adjusting instruction. In some embodiments, the examination table control module 330 may receive an examination table speed adjusting instruction generated by the processing module 310 or inputted by a user. The examination table control module 330 may control the examination table 140 to move or adjust the moving speed of examination table 140 along the Z-axis direction according to the information relating to the preset moving speed of the examination table speed adjusting instruction.

The data acquisition module 340 may receive external data or information inputted by a user. Functions of the data acquisition module 340 may be achieved by the processor 220 in FIG. 2. In some embodiments, the data acquisition module 340 may transmit the received data/information to the processing module 310 for processing. In some embodiments, the data acquisition module 340 may transmit the received data/information to the slice control module 320 or the examination table control module 330. The slice control module 320 or the examination table control module 330 may control units thereof according to the received data/information. In some embodiments, the data acquisition module 340 may transmit the received data/information to the storage module 370. In some embodiments, the data acquisition module 340 may receive an instruction for acquiring data (also referred to herein as data acquisition instruction) from the processing module 310. The data acquisition module 340 may acquire data/information according to the data acquisition instruction. In some embodiments, the data acquisition module 340 may receive external data. The data acquisition module 340 may transmit the external data to the processing module 310 for numerical computation of target parameters. For example, the data acquisition module 340 may receive scanning data obtained by the detector 150 and transmit the scanning data to the processing module 310 for further calculation and processing. In some embodiments, the data acquisition module 340 may preprocess the scanning data after the acquisition of scanning data.

The image reconstruction module 350 may reconstruct a medical image.

Functions of image reconstruction module 350 may be achieved by the processor 220 in FIG. 2. In some embodiments, the image reconstruction module 350 may receive data/information from the processing module 310 or the storage module 370. The image reconstruction module 350 may reconstruct the medical image based on the received data/information. Further, the medical image may be a three dimensional medical image of a human body. In some embodiments, the image reconstruction module 350 may receive data from the processing module 310 or the storage module 370. The data may include scanning data at different times, different positions, or different angles. The image reconstruction module 350 may determine a feature or status, e.g., the absorption coefficient of X-rays, a tissue density, etc., of a corresponding part of the human body based on the received scanning data. Then the image reconstruction module 350 may reconstruct the medical image of the human body based on the received scanning data. Further, the display module 360 may display the three dimensional medical image of the human body. The storage module 370 may store the reconstructed three dimensional medical image.

The display module 360 may display data/information. Functions of the display module 360 may be achieved by the display 280 in FIG. 2. In some embodiments, the display module 360 may display the three dimensional medical image of the human body generated by the image reconstruction module 350. In some embodiments, the display module 360 may display the data or instructions generated by the processing module 310. In some embodiments, the display module 360 may display the information obtained by the data acquisition module 340. The information may include but not limited to information relating to the measurement data of the detector 150, information relating to the work status of the scanning system 100, or information relating to the instructions generated by the processing module 310. In some embodiments, the information displayed by the display module 360 may include but not limited to light, words, sound, images, etc.

In some embodiments, the display module 360 may include physical display equipment, e.g., a display with a loud speaker, a Liquid Crystal Display (LCD), a light-emitting diode (LED) display, an Organic Light Emitting Diode (OLED) display, an electronic ink display (E-Ink), etc. In some embodiments, the display module 360 may receive a feedback and transmit the feedback to the processing module 310. Further, the processing module 310 may generate a control instruction based on the feedback. For example, when the display module 360 receives the feedback, the display module 360 may display that "the examination table has arrived at the target position, whether or not to activate the radiation device?" The processing module 310 may generate instructions for activating a corresponding device after a user feedback for, e.g., activating the device, is received.

The storage module 370 may store information or data. Functions of the storage module 370 may be achieved by a combination of at least one of the hard disk 270, the ROM 230, and the RAM 240 in FIG. 2. The storage module 370 may store information of a module or device inside or outside of the control and processing system 160. In some embodiments, the storage module 370 may transmit the stored information to the processing module 310 for processing. In some embodiments, the storage module 370 may store information generated by the processing module 310. In some embodiments, the information stored in the storage module 370 may include information relating to a scan by the detector 150, information relating to instructions or parameters inputted by a user, immediate data or complete data generated by the processing module 310, or the like, or any combination thereof. In some embodiments, the storage module 370 may include but not limited to all kinds of storage devices, e.g., a Solid State Disk (SSD), a Hard Disk Drive (HDD), a flash memory with Universal Serial Bus (USB), a Secure Digital Card (SD card), an optical disk, a Radom Access Memory (RAM), a Read Only Memory (ROM), etc. In some embodiments, the storage module 370 may be a storage device inside the system 100 or a storage device that is external to or as an add-on of the system 100, e.g., storage on a cloud storage server.

Figure 4:
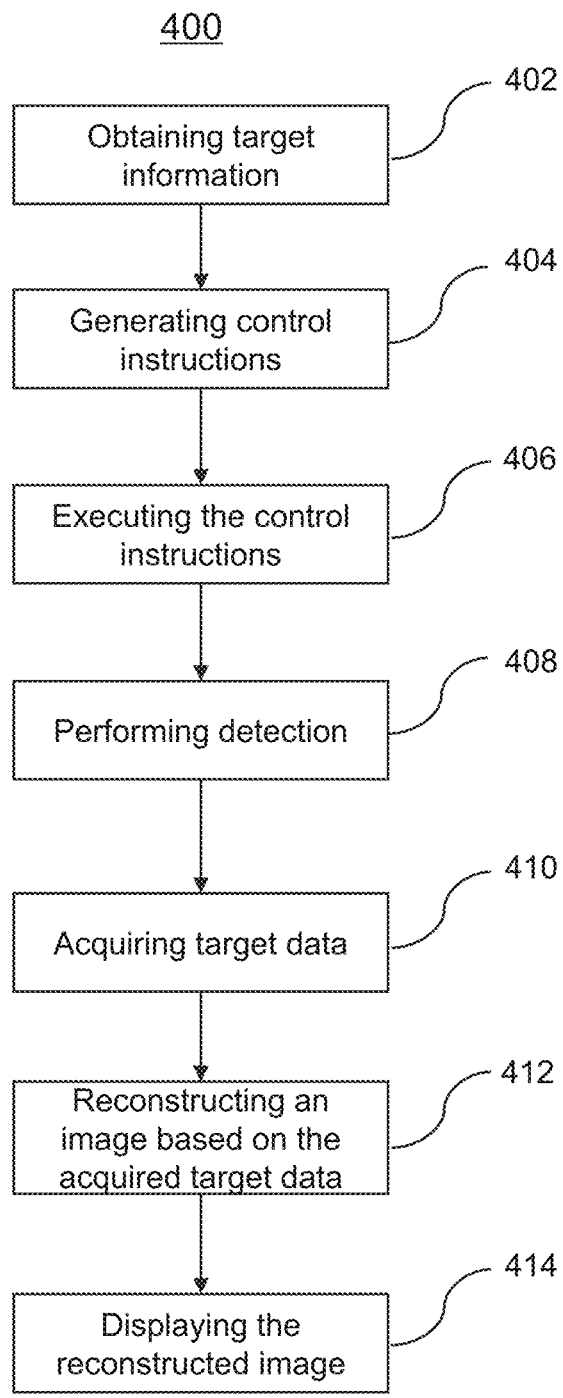
FIG. 4 is a flowchart of an exemplary process for operating the scanning system according to some embodiments of the present disclosure.

FIG. 4 is a flowchart of an exemplary process for operating the scanning system according to some embodiments of the present disclosure. In 402, target information may be obtained. In some embodiments, the target information may be information obtained by data acquisition module 340 or inputted by a user. Further, the target information obtained by data acquisition module 340 may include information relating to the position of the examination table 140, information relating to the work status of the system, and information relating to system parameters, etc. The target information inputted by a user may include information relating to parameter setting, control information, etc.

In 404, control instructions may be generated based on the target information generated in 402. The control instructions may include slice control instructions, examination table control instructions, radiation device activation instructions, etc. The slice control instructions may include slice position adjusting instructions or angle adjusting instructions (detailed descriptions of the slice control instructions, the examination table control instructions, and the radiation device control instructions may be found in FIG. 3 and relevant descriptions thereof).

In 406, one or more control operations may be executed based on the control instructions generated in 404. In some embodiments, the examination table control module 330 may obtain the examination table control instructions generated in 404. The examination table control module 330 may adjust the position of the examination table 140 based on the examination table control instructions. In some embodiments, the slice control module 320 may obtain the slice position adjusting instructions generated in 404 to adjust the position of the slice module. In some embodiments, the slice control module 320 may obtain the angle adjusting instructions generated in 404 and control the rotation of the drum in slice module according to the angle adjusting instructions. In some embodiments, the radiation device 120 may obtain the radiation device activation instructions generated in 404 to activate the radiation device 120. In some embodiments, the radiation device 120 may obtain the radiation device activation instructions in 404 and/or 406 to perform a detection accordingly, e.g., in 408.

In 410, the detector 150 may acquire target data and transmit the acquired target data to the processing module 310 for processing. The target data may include scanning data at different times, different positions, or different angles. In 412, the processing module 310 may process the target data. The image reconstruction module 350 may generate a medical image based on the processed target data. In 414, the display module 360 may receive the medical image generated in 412 and display the medical image.

Figure 5:
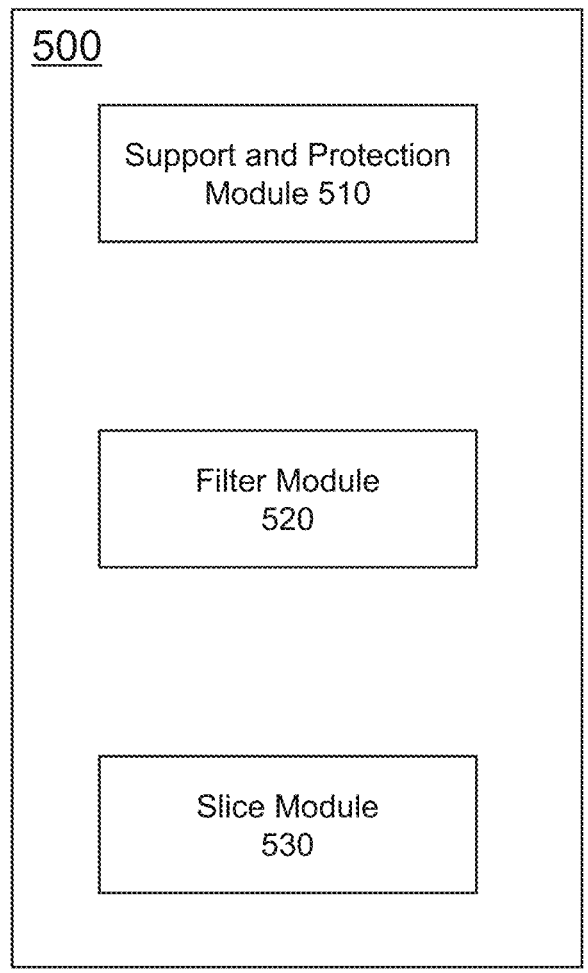
FIG. 5 is a block diagram illustrating an exemplary collimator according to some embodiments of the present disclosure.

FIG. 5 is a block diagram illustrating an exemplary collimator according to some embodiments of the present disclosure. The collimator 500 may be settled between the examination table 150 and the radiation device 120. The collimator 500 may include a support and protection module 510, a filter module 520, and a slice module 530 (FIG. 10 and relevant descriptions thereof provide an exemplary schematic diagram and description of the collimator 500). The support and protection module 510 may be configured to support the whole structure of and provide a partial protection to the collimator 500. The filter module 520 may be configured to filter rays passing through the collimator 500 to reduce harm to the human body. Further, the filter module 520 may include one or more filters. The one or more filters may have different filtering parameters. Different filters may be selected according to different detection needs during a detection process. The slice module 530 may adjust the fan-beam width of the rays that pass through the collimator 500. In some embodiments, the radiation device 120 may generate rays. The generated rays may pass through the slice module 530 and the filter module 520 in sequence. The slice module 530 may adjust the fan-beam width of the rays. The filter module 520 may adjust the intensity of the rays. In some embodiments, the support and protection module 510 may have a box structure with a top opening and a side opening. The filter module 520 may be placed into the support and protection module 510 from the side opening. The slice module 530 may be placed into the support and protection module 510 from the top opening.

Figure 6:
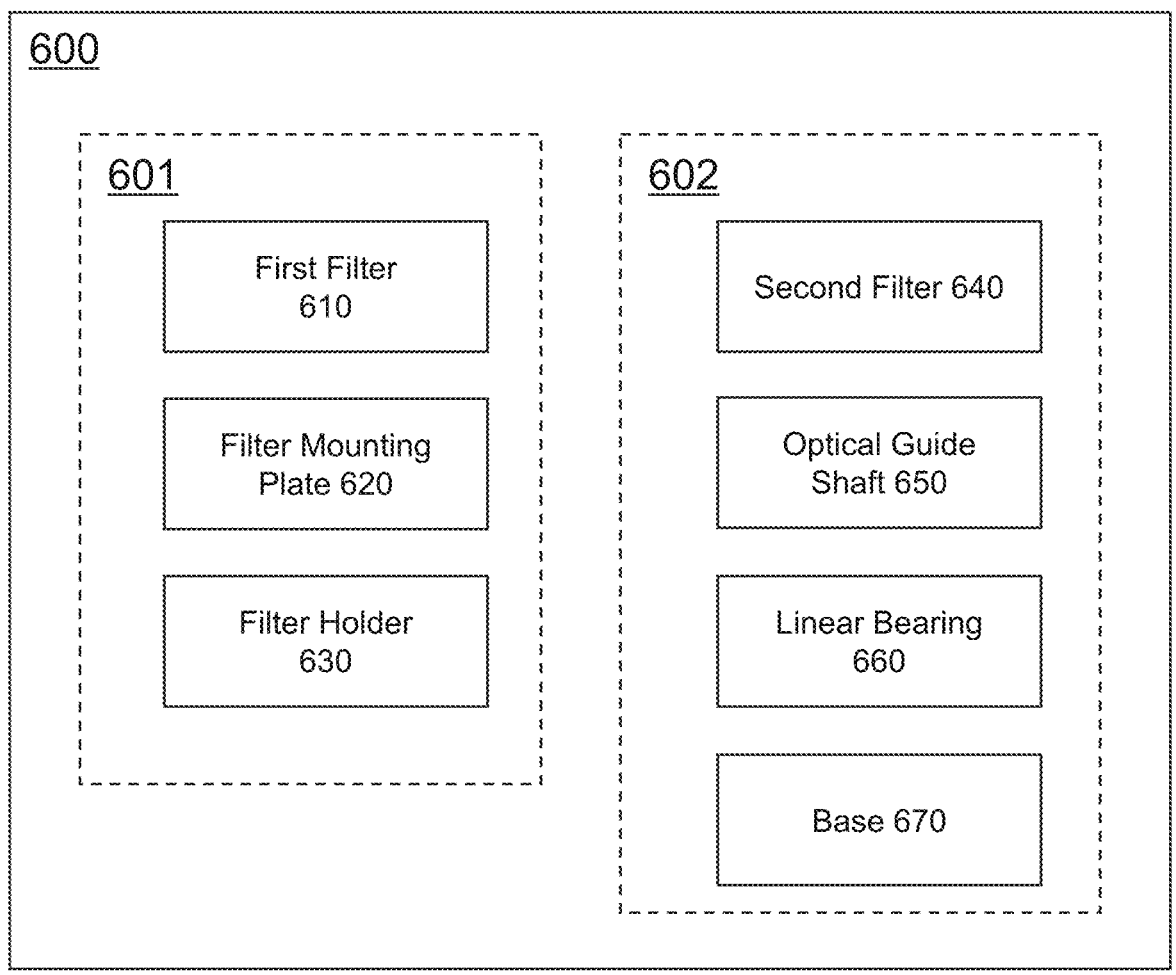
FIG. 6 is a block diagram illustrating an exemplary filter module according to some embodiments of the present disclosure.

FIG. 6 is a block diagram illustrating an exemplary filter module according to some embodiments of the present disclosure. As shown in FIG. 6, the filter module 600 may include a filter replacing unit 601 and a filter floating base 602 (FIG. 11 and relevant descriptions thereof provide an exemplary schematic diagram and description of the filter module 600). In some embodiments, the filter replacing unit 601 may be detachably mounted on filter floating base 602. The filter replacing unit 601 may include one or more first filters 610, a filter mounting plate 620, and a filter holder 630. The one or more first filters 610 may be mounted on the filter mounting plate 620 via the filter holder 630. In some embodiments, the one or more first filters 610 may be arranged side by side along the direction that the filter floating base 602 may move along. Further, the one or more first filters 610 may include various filters of different parameters, e.g., a body filter, a head filter, a baby filter, etc. A body filter may have a relative low filtering capacity so that a high radiation intensity may be retained to generate images of high quality of a body or an area of multiple overlapping organs. A head filter (e.g., the first head filter) may have a relative high filtering capacity so that it may well protect the brain during a detection process. A baby filter may have the highest filtering capacity among these filters, and it may minimize damage to tissue or organs of a baby during a detection process. In some embodiments, the one or more first filters 610 may include a butterfly filter, a plate filter, or a combination thereof.

The filter floating base 602 may include one or more second filters 640, an optical guide shaft 650, a linear bearing 660, and a base 670. In some embodiments, the linear bearing 660 and the second filters 640 may be placed on the base 670. Further, the optical guide shaft 650 may rotate and drive the base 670 to move along the axial direction of the optical guide shaft. In some embodiments, the one or more second filters 640 may be arranged side by side along the axial direction of the optical guide shaft. Further, the one or more second filters 640 may include various filters of different parameters, e.g., a body filter, a head filter, a baby filter, etc. In some embodiments, the one or more second filters 640 may include a butterfly filter, a plate filter, or a combination thereof. In some embodiments, the second filters 640 of the filter floating base 602 and the first filters 610 of the filter replacing unit 601 may be of the same type. The count of the second filters 640 of the filter floating base 602 may be the same as the count of the first filters 610 of the filter replacing unit 601. The second filters 640 of the filter floating base 602 and the first filters 610 of the filter replacing unit 601 may be arranged in one-to-one correspondence. In some embodiments, rays generated by the radiation device 120 may strike on g the collimator 1000 and pass through the first filters 610 and the corresponding second filters 640 in order. Further, the filter floating base 602 may include a focus measuring plate. The focus measuring plate may be mounted on the base 670. In some embodiments, the focus measuring plate may measure the size of the focus when the scanning system 100 performs correction on an image, which may improve the measurement accuracy of the scanning system 100.

Figure 7:
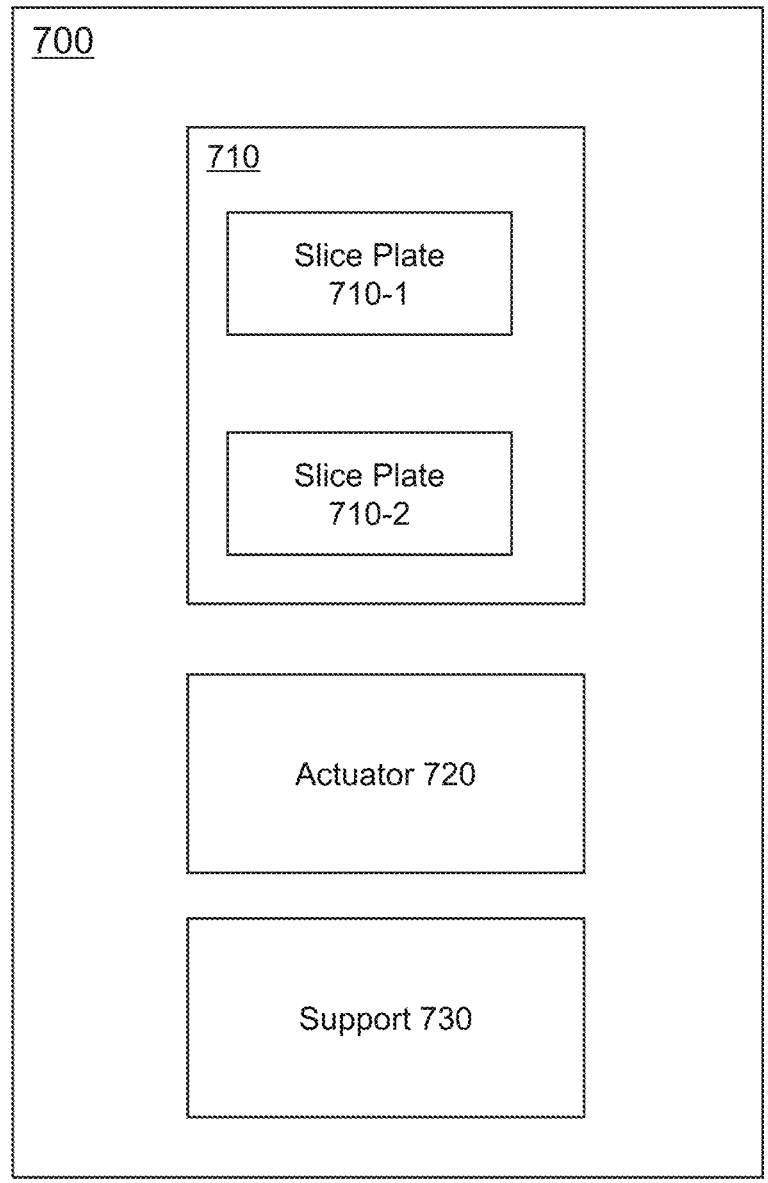
FIG. 7 is a block diagram of an exemplary slice module according to some embodiments of the present disclosure.

FIG. 7 is a block diagram of an exemplary slice module according to some embodiments of the present disclosure. The slice module 700 may correspond to the slice module 530 shown in FIG. 5. As shown in FIG. 7, the slice module 700 may include a slice plate unit 710, an actuator 720, and a support 730. (FIG. 12a and relevant descriptions thereof provide an exemplary schematic diagram and description of the slice module 700). The slice plate unit 710 and the actuator 720 after being assembled may be placed on the support 730. In some embodiments, the slice plate unit 710 may include a first slice plate 710-1 and a second slice plate 710-2. An opening may be formed between the first slice plate 710-1 and the second slice plate 710-2. In some embodiments, the radiation device 120 may generate rays. The rays may pass through the opening of the slice plate unit 710. The rays may be blocked or absorbed in other parts of the slice plate unit 710. Further, the fan-beam width of the rays passing through the opening may depend on the size of the opening. In some embodiments, the actuator 720 may adjust the size of the opening by controlling the movement of the slice plate 710-1 and the slice plate 710-2 to adjust the fan-beam width of the rays.

Figure 8:
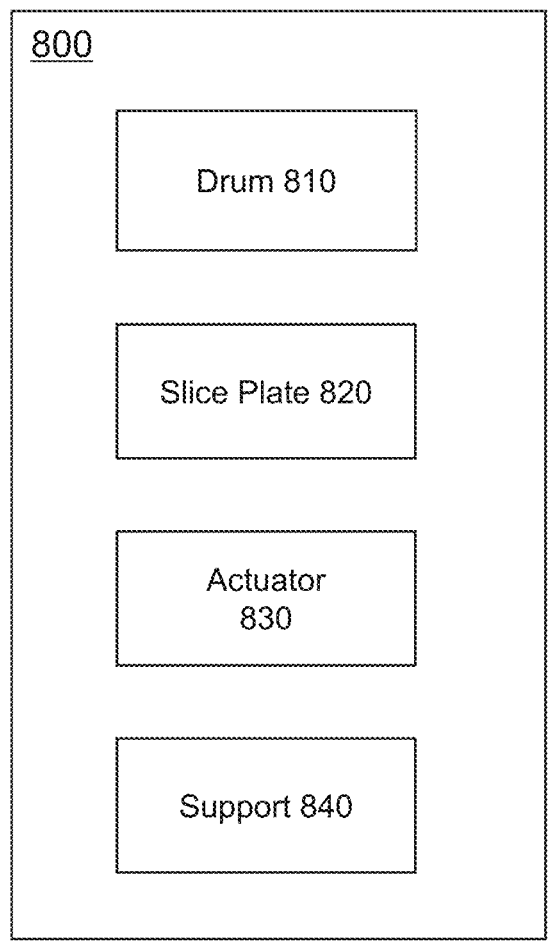
FIG. 8 is a block diagram of another exemplary slice module according to some embodiments of the present disclosure.

FIG. 8 is a block diagram of an exemplary slice module according to some embodiments of the present disclosure. The slice module 800 may correspond to the slice module 530 shown in FIG. 5. As shown in FIG. 8, the slice module

800 may include a drum 810, one or more slice plates 820, an actuator 830, and a support 840. (FIG. 13 and relevant descriptions thereof provide an exemplary schematic diagram and description of the slice module 800). In some embodiments, the slice plate 820 may be placed on the lateral surface of the drum. The drum 810 and the actuator 830 after being assembled may be placed on the support 840. In some embodiments, the one or more slice plates 820 may include one or more openings. Further, the openings may be different in terms of size and shape. In some embodiments, the radiation device 120 may generate rays. When passing through the one or more slice plates 820, the rays may pass through the one or more openings, and be blocked or absorbed in other parts of the the one or more slice plates 820. In some embodiments, different slice plates 820 may be selected through changing the angle of the drum 810, which may adjust or modify the width and the position of the fan-beam of the rays.

Figure 9:
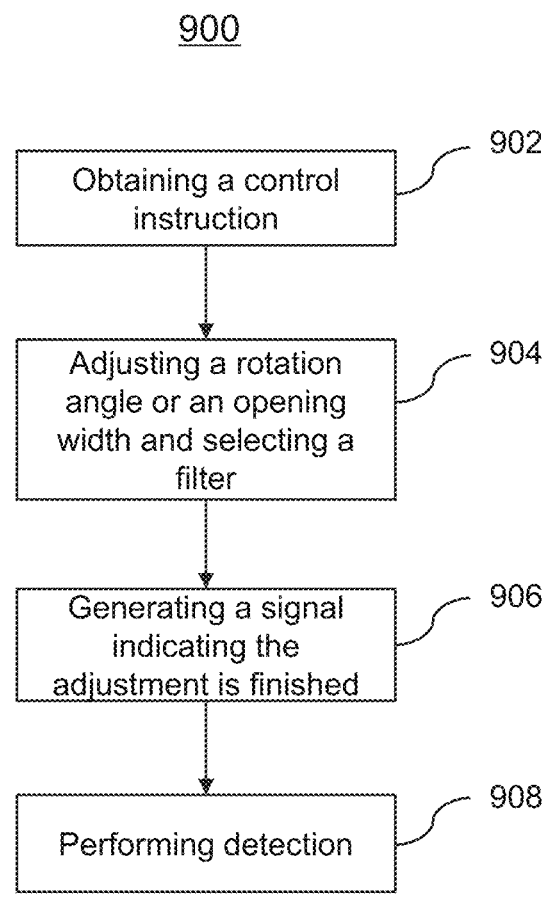
FIG. 9 is a flowchart illustrating an exemplary process for adjusting a collimator according to some embodiments of the present disclosure.

FIG. 9 is a flowchart of an exemplary process for adjusting the collimator according to some embodiments of the present disclosure. In 902, a control instruction may be obtained. The control instruction may be from the processing module 310. The control instruction may include a slice position adjusting instruction, an opening size adjusting instruction, an angle adjusting instruction, and/or a filter selecting instruction, etc. The slice position adjusting instruction may be used to adjust the position of the slice module 530. The opening size adjusting instruction may be used to adjust the size of the opening between the slice plates (e.g., the first slice plate 1225-2 and the second slice plate 1230-2 shown in FIG. 12). The angle adjusting instruction may be used to adjust the rotation angle of the drum 810. The filter selecting instruction may be used to select a filter type of the first filters 610 and/or the second filters 640 of the filter module 520. The filter type may include a body filter, a head filter, a baby filter, etc.

In 904, the components or units of the filter module 520 and/or the slice module 530 may be adjusted based on the control instruction obtained in 902. For example, in 904, the slice plate unit 710 may be adjusted via the actuator 720 to determine the size of the opening between the slice plate 710-1 and the slice plate 710-2. In 904, the angle of the drum 810 may also be adjusted via the actuator 830 to select a slice plate 820 with an opening of a desired size. In 904, the filter type(s) of the first filters 610 and/or the second filters 640 may also be selected through rotating the optical guide shaft 650. The filter type may include a body filter, a head filter, a baby filter, etc.

After the adjustment described in 904 is finished, a signal indicating the adjustment is finished (also referred to herein as an adjustment completion signal) may be generated in 906. The adjustment completion signal may be transmitted to the processing module 310. The processing module 310 may generate a radiation device activation instruction and transmit the radiation device activation instruction to the radiation device 120 after receiving the adjustment completion signal. The radiation device 120 may perform detection in 908 once receiving the radiation device activation instruction. In some embodiments, operation 908 may correspond to operation 408.

Figure 10A:
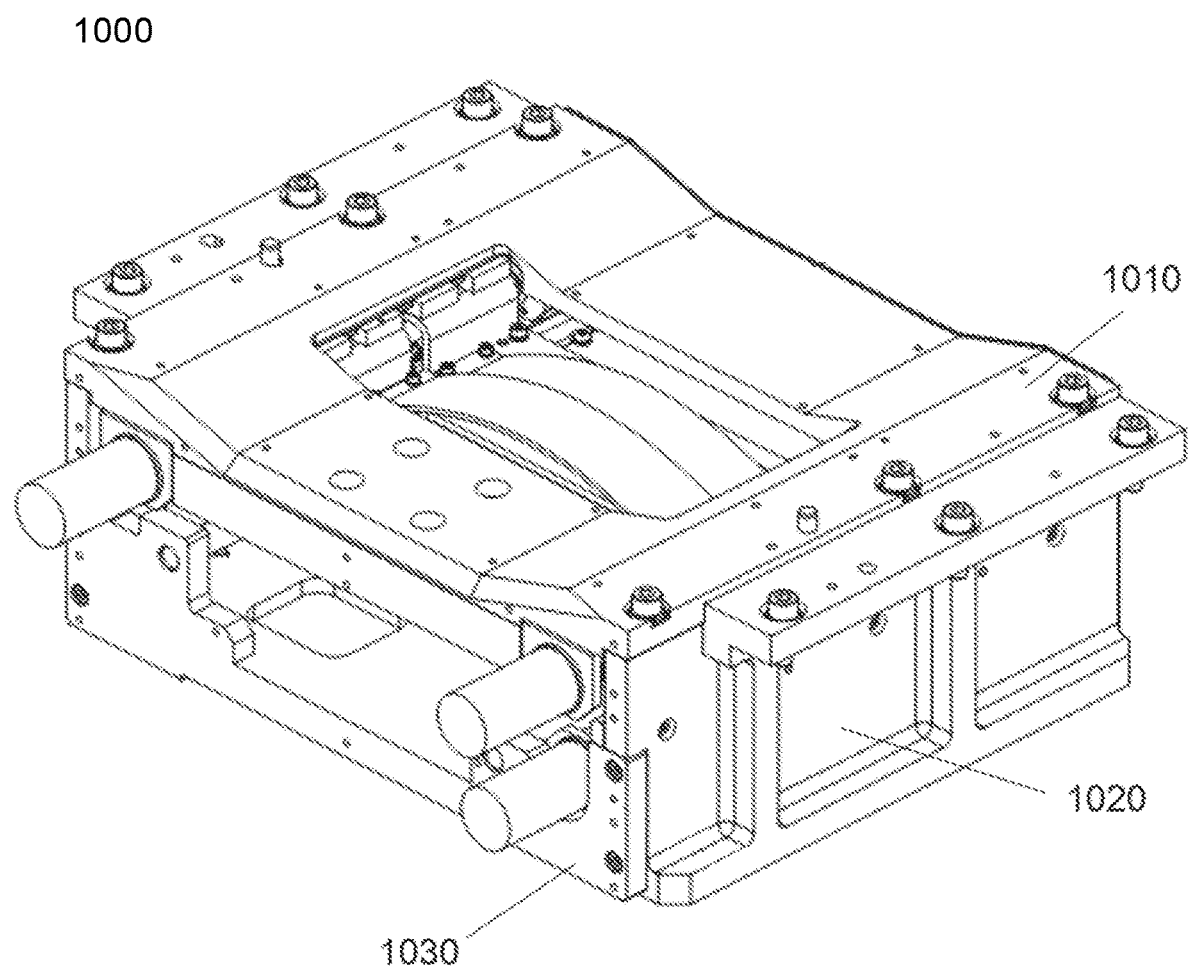
FIG. 10a is a schematic diagram of an exemplary collimator according to some embodiments of the present disclosure.

FIG. 10*a* is a schematic diagram of an exemplary collimator according to some embodiments of the present disclosure. The collimator 1000 (corresponding to the collimator 130) may filter or block the rays or adjust the fan-beam width of the rays generated by the radiation device 120 of the scanning system 100. The collimator 1000 may include a slice module 1010, a support and protection module 1020, and a filter module 1030 (corresponding to the slice module 530, the support and protection module 510, and the filter module 520 in FIG. 5, respectively). The filter module 1030 and the slice module 1010 may be detachably connected with the support and protection module 1020. In some embodiments, the rays may strike on the collimator 1000 and pass through the slice module 1010 and the filter module 1030 in order. The slice module 1010 may adjust the fan-beam width of the rays. The filter module 1030 may filter the rays in different ways by the filters of different types. Further, the adjustment of the fan-beam width and the filtering may satisfy scanning conditions for different detection objects.

Figure 10B:
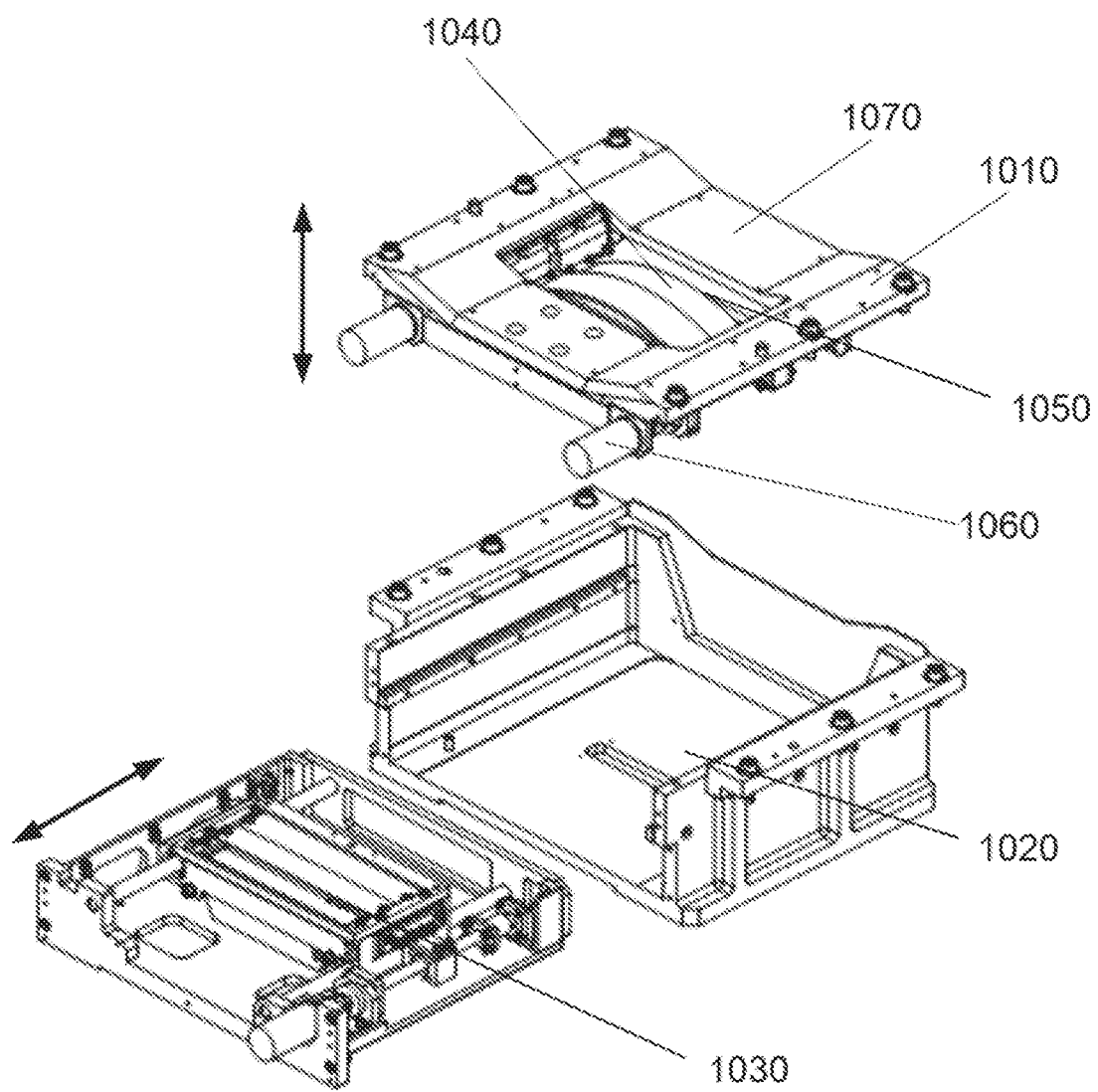
FIG. 10b is a partially exploded view of an exemplary collimator according to some embodiments of the present disclosure.

FIG. 10*b* is a partially exploded view of an exemplary collimator according to some embodiments of the present disclosure. As shown in FIG. 10*b*, a slice module 1010, a support and protection module 1020, and a filter module 1030 of the collimator 1000 may be detachably connected together. In some embodiments, the support and protection module 1020 may have a box structure with a top opening and a side opening. Further, the filter module 1030 may be placed into the support and protection module 510 from the side opening or the top opening. For example, the filter module 1030 may be placed into and pulled from the box structure from the side opening of the box structure. The slice module 1010 may be mounted on the box structure from the top opening and close the top opening. The structures of the slice module 1010, the support and protection module 1020, and the filter module 1030 may keep the components from interfering with each other. The structures may also facilitate the blocking of rays through a protective shield outside of the filter module 1030 and the slice module 1010, which may enhance the function of protection by blocking rays of the support and protection module 1020. Further, the slice module 1010 may include a slice plate 1040 and a slice plate 1050 arranged side by side, an actuator 1060, and a support 1070 (details of structures of the slice plate 1040, the slice plate 1050, the actuator 1060, and the support 1070 may be found in FIG. 12*a* and relevant descriptions thereof).

Figure 11A:
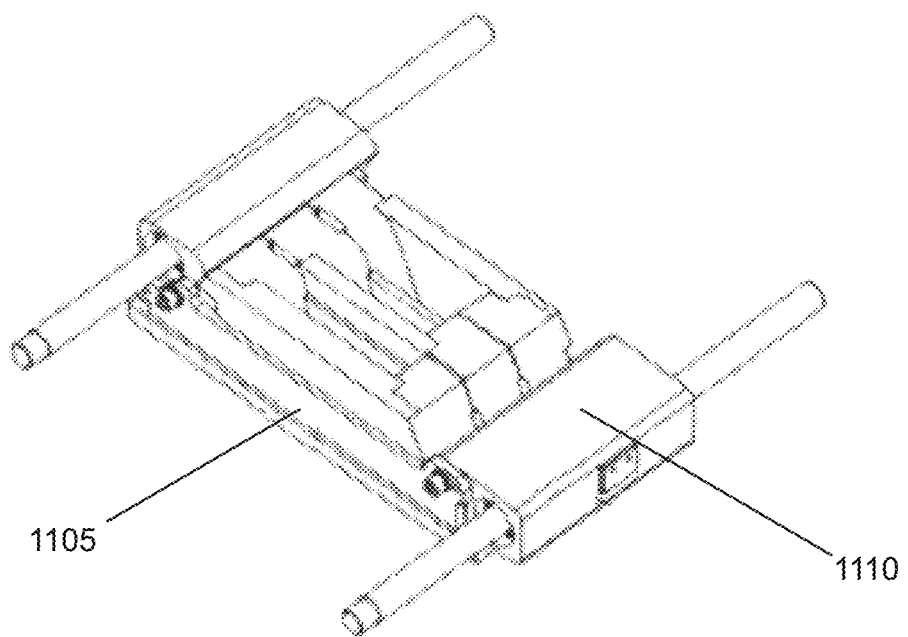
FIG. 11a is a schematic diagram of an exemplary filter module according to some embodiments of the present disclosure.

FIG. 11*a* is a schematic diagram of an exemplary filter module according to some embodiments of the present disclosure. The filter module 1030 may correspond to the filter module 600 in FIG. 6. As shown in FIG. 11*a*, the filter module 1030 may include a filter replacing unit 1105 and a filter floating base 1110. In some embodiments, the filter replacing unit 1105 may be detachably connected with the filter floating base 1110. For example, the filter floating base 1110 may be placed on one side of the support and protection module 1020 and pulled from the support and protection module 1020. In some embodiments, different filtering needs may be satisfied just by pulling out the filter floating base 1110 and replacing the filter replacing unit 1105 or the first filters 1145 of the filter replacing unit 1105.

Figure 11B:
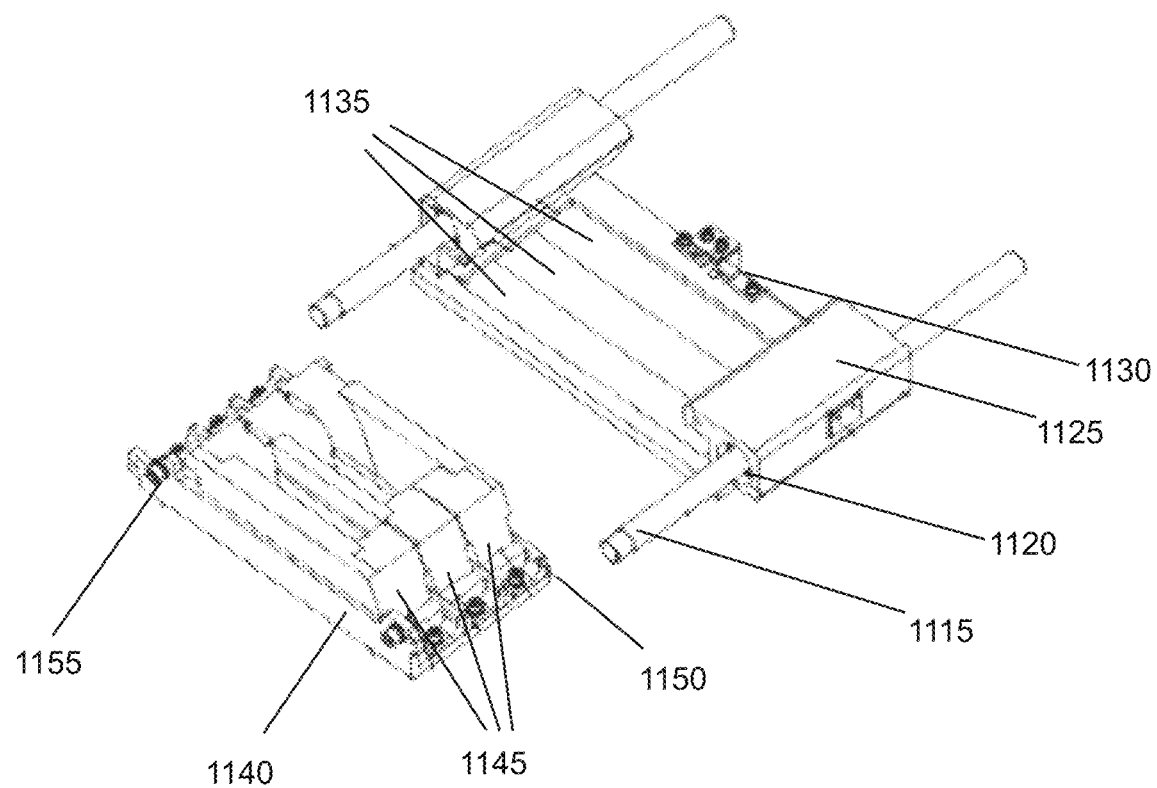
FIG. 11b is a partially exploded view of an exemplary filter module according to some embodiments of the present disclosure.

FIG. 11*b* is a partially exploded view of an exemplary filter module according to some embodiments of the present disclosure. As shown in FIG. 11*b*, the filter replacing unit 1105 and the filter floating base 1110 of the filter module 1030 may be detachably connected together. Further, the filter replacing unit 1105 may include one or more first filters 1145, a filter mounting plate 1150, and a filter holder 1140. The first filters 1145 may be mounted on the filter mounting plate 1150 through the filter holder 1140. In some embodiments, the one or more first filters 1145 may be arranged side by side along the direction that the filter floating base 1110 may move along. In some embodiments, the one or more first filters 1145 may include various filters of different parameters, e.g., a body filter, a head filter, a baby filter, etc. In some embodiments, the first filter(s) 1145 may include a butterfly filter, a plate filter, or a combination thereof.

The filter floating base 1110 may include one or more second filters 1135, an optical guide shaft 1115, a linear gearing 1120, and a base 1125. Further, the linear gearing 1120 and the second filters 1135 may be fixed on the base 1125. The optical guide shaft 1115 may be located in the linear gearing 1120. In some embodiments, the optical guide shaft 1115 may rotate and drive the base 1125 to move along an axial direction of the optical guide shaft 1115. In some embodiments, the one or more second filters 1135 may be arranged side by side along the axis direction of the optical guide shaft 1115. Further, the one or more second filters 1135 may include various filters of different parameters, e.g., a body filter, a head filter, a baby filter, etc. In some embodiments, the first filter(s) 1145 may include a butterfly filter, a plate filter, or a combination thereof. In some embodiments, the second filter(s) 1135 of the filter floating base 1110 and the first filter(s) 1145 of the filter replacing unit 1105 may be of the same type. The count of the second filter(s) 1135 of the filter floating base 1110 may be the same as the count of the first filter(s) 1145 of the filter replacing unit 1105. The second filter(s) 1135 of the filter floating base 1110 and the first filter(s) 1145 of the filter replacing unit 1105 may be arranged in one-to-one correspondence. For example, the count of the second filter(s) 1135 may be three, while the count of the first filter(s) may also be three. For example, the second filter(s) may be plate head filter(s), while the first filter(s) may also be plate head filter(s). In some embodiments, rays generated by the radiation device 120 after striking on the collimator 1000 (corresponding to the collimator 130) may pass through the first filter(s) 1145 and the second filter(s) 1135 in order. Further, the filter floating base 1110 may also include a focus measuring plate 1130. The focus measuring plate 1130 may measure the size of the focus which may be used when the scanning system 1000 performs correction on an image, thereby improving the measurement accuracy of the scanning system.

Figure 12A:
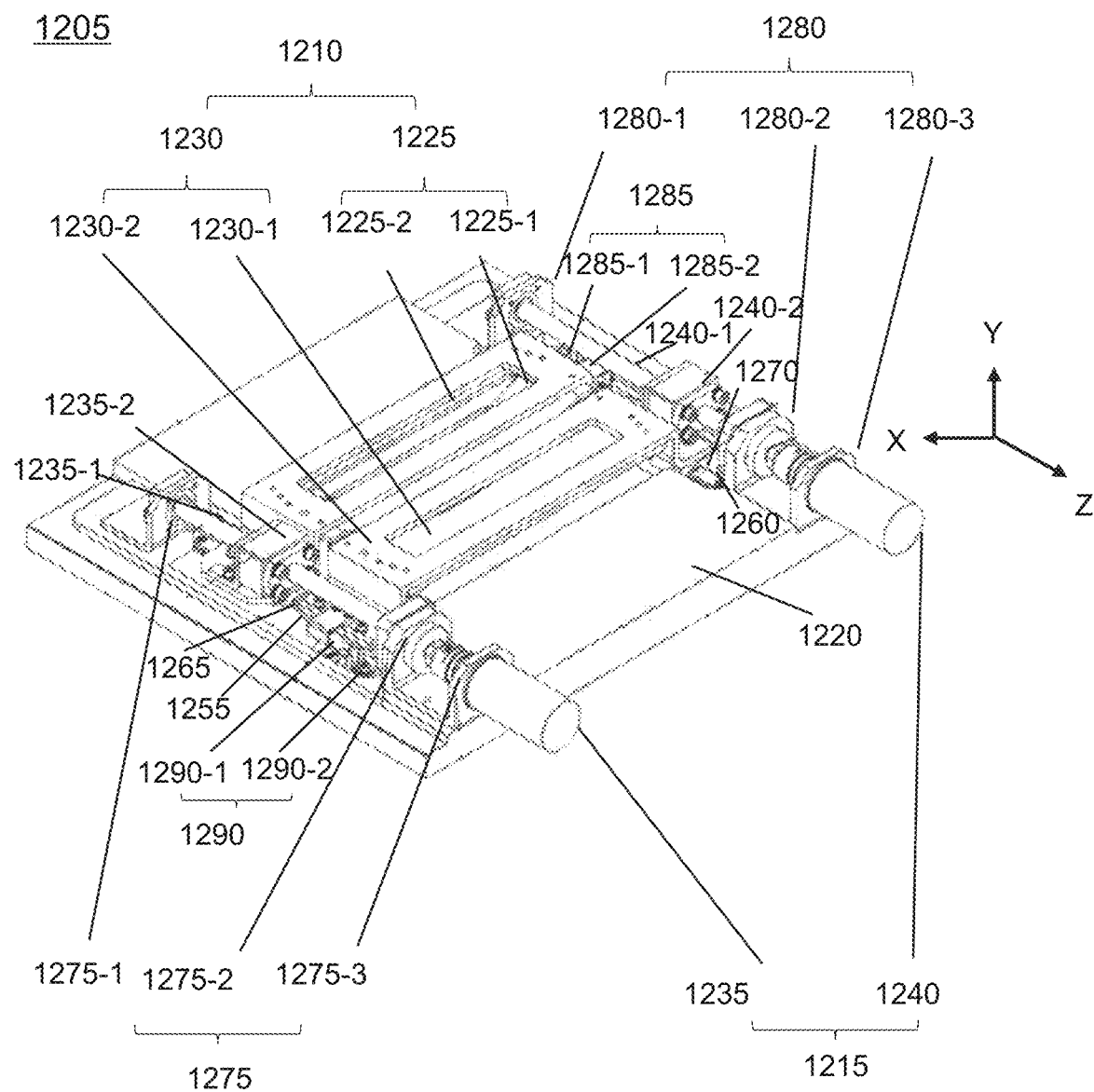
FIG. 12a is a schematic diagram of an exemplary slice module according to some embodiments of the present disclosure.

FIG. 12a is a schematic diagram of an exemplary slice module according to some embodiments of the present disclosure. The slice module 1205 may correspond to the slice module 700 in FIG. 7. As shown in FIG. 12a, the slice module 1205 may include a slice plate unit 1210, an actuator 1215, and a support 1220. The slice plate unit 1210 and the actuator 1215 may be detachably assembled and mounted on the support 1220. Further, the slice plate unit 1210 may include a first slice plate component 1225 and a second slice plate component 1230. The actuator 1215 may include a first actuator 1235 corresponding to the first slice plate component 1225. The actuator 1215 may also include a second actuator 1240 corresponding to the second slice plate component 1230.

Further, the first slice plate component 1225 may include a first slice holder 1225-1 and a first slice plate 1225-2. The first slice plate 1225-2 may be fixed on the first slice plate holder 1225-1. The second slice plate component 1230 may include a second slice plate holder 1230-1 and a second slice plate 1230-2. The second slice plate 1230-2 may be fixed on the second slice plate holder 1230-1. In some embodiments, the first slice plate component 1225 and the second slice plate component 1230 may have the same structure.

Further, a space may exist between the first slice plate 1225-2 and the second slice plate 1230-2. The space may form an opening. In some embodiments, the width of the rays (e.g., the fan-beam width of the rays) passing through the opening may be adjusted by changing the size of the opening. In some embodiments, the slice plate unit 1210 may further include a first position block 1245 and a second position block 1250. The first position block 1245 may be fixed on the first slice plate holder 1225-1. The first position block 1245 and the first slice plate 1225-2 may be arranged along the Z-axis direction. The second position block 1250 may be fixed on the second slice plate holder 1230-1. The second position block 1250 and the second slice plate 1230-2 may be arranged along the Z-axis direction. In some embodiments, an adjustment gap may be preserved between the first position block 1245 and the first slice plate 1225-2, and an adjustment gap between the second position block 1250 and the second slice plate 1230-2, to allow an alignment of the first slice plate 1225-2 and the second slice plate 1230-2 relative to the detector 140 along the Z-axis direction during assembly.

In some embodiments, the first actuator 1235 and the second actuator 1240 may have the same structure. The first actuator 1235 and the second actuator 1240 may control the first slice plate component 1225 and the second slice plate component 1230, respectively, to move along the Z-axis direction. Further, the first actuator 1235 and the second actuator 1240 may have a screw-nut gearing, a linear bearing gearing, a turbo-worm gearing, a pinion and rack gearing, or the like, or a combination thereof. In some embodiments, the first actuator 1235 may include a first ball screw 1235-1 mounted on the support 1220. The first actuator 1235 may also include a first screw nut base 1235-2 coupled with the first ball screw 1235-1. The first screw nut base 1235-2 may be fixedly connected with the first slice plate holder 1225-1. The second actuator 1240 may include a second ball screw 1240-1 mounted on the support 1220. The second actuator 1240 may also include a second screw nut base 1240-2 coupled with the second ball screw 1240-1. The second screw nut base 1240-2 may be fixedly connected with the second slice plate holder 1230-1.

In some embodiments, the first ball screw 1235-1 and the second ball screw 1240-1 may have threads. The first screw nut base 1235-2 and the second screw nut base 1240-2 may have threaded holes. The threaded holes may correspond to the threads. In some embodiments, the structures of the first actuator 1235 and the second actuator 1240 may cause the rotation of the first ball screw 1235-1 and the second ball screw 1240-1 to be transformed to a linear movement of the first screw nut base 1235-2 and the second screw nut base 1240-2, respectively. For example, the rotation of the first ball screw 1235-1 and the second ball screw 1240-1 may drive the first screw nut base 1235-2 and the second screw nut base 1240-2 to move along a straight line in the Z-axis direction, which may cause the size of the opening between the first slice plate 1225-2 and the second slice plate 1230-2 to be adjustable.

In some embodiments, either of the first slice plate holder 1225-1 and the second slice plate holder 1230-1 may include a first end and a second end. The first end may be opposite to the second end. The first screw nut base 1235-2 may be connected with the first end of the first slice plate holder 1225-1. The second screw nut base 1240-2 may be connected with the second end of the second slice plate holder 1230-1. Further, the first slice plate holder 1225-1 may be connected with the first slice plate 1225-2 and the first actuator 1235, while the second slice plate holder 1230-1 may be connected with the second slice plate 1230-2 and the second actuator 1240. When the structures of the first actuator 1235 or the second actuator 1240 need to change, it only need to change the structures of the first slice plate holder 1225-1 or the second slice plate holder 1230-1 without changing or replacing the first slice plate 1225-2 or the second slice plate 1230-2. The structures of the first slice plate 1225-2 or the second slice plate 1230-2 (e.g., the shape/size of an opening, etc.) may be changed when needed by only changing or replacing the first slice plate 1225-2 or the second slice plate 1230-2 without changing the structures of the first actuator 1235, the second actuator 1240, the first slice plate holder 1225-1, or the second slice plate holder 1230-1, thereby improving the adaptability and the reusability of the slice module.

In some embodiments, the support 1220 may include a plate with a hollow part. The hollow part may correspond to the first slice plate 1225-2 and the second slice plate 1230-2. In some embodiments, the hollow structure of the support 1220 may reduce the weight of the slice module 1205, which may also reduce a centrifugal force on the slice module 1205 during a scan. Further, other components of the slice module 1205 (e.g., the first actuator 1235 and/or the second actuator 1240) may be placed in the hollow part of the support 1220 to save space. In some embodiments, the first slice plate component 1225, the second slice plate component 1230, the first actuator 1235, and the second actuator 1240 may be mounted on the support 1220. The configuration may make it easy to assemble and disassemble the slice plate unit 1210 and the actuator 1215, and to precisely position the slice module 1205 during assembly. Therefore, the alignment of the slice module 1205 and the detector 140 along the Z-axis direction may be realized.

A first linear guide 1255 and a second linear guide 1260 may be mounted on the support 1220. Further, a first slider 1265 coupled with the first linear guide 1255 and a second slider 1270 coupled with the second linear guide 1260 may also be mounted on the support 1220. In some embodiments, the first slider 1265 may be connected with the first end of the first slice plate holder 1225-1, and the second slider 1270 may be connected with the second end of the second slice plate holder 1230-1. In some embodiments, the cooperation of the linear guides and the sliders may drive the first slice plate component 1225 and the second slice plate component 1230 to move along the linear guides.

Further, a first support base 1275 and a second support base 1280 may be oppositely mounted on the support 1220. In some embodiments, the first support base 1275 may be configured to support the first ball screw 1235-1. Further, the first support base 1275 may include three supporting plates 1275-1, 1275-2, and 1275-3 arranged along the Z-axis direction. Each of the three supporting plates 1275-1, 1275-2, and 1275-3 may include a holding aperture to hold the first ball screw 1235-1. The second support base 1280 may be configured to support the second ball screw 1240-1. Further, the second support base 1280 may include three supporting plates 1280-1, 1280-2, and 1280-3 arranged along the Z-axis direction. Each of the three supporting plates 1280-1, 1280-2, and 1280-3 may include a holding aperture to hold the second ball screw 1240-1.

In some embodiments, the slice module 1205 may further include a first position limiting block 1285 and a second position limiting block 1290. The first position limiting block 1285 may be configured to detect whether the first slice plate holder 1225-1 has returned to a preset position. In some embodiments, the preset position may be a starting position (also referred to herein as a zero position). Correspondingly, the second position limiting block 1290 may be configured to detect whether the second slice plate holder 1230-1 has returned to a preset location.

In some embodiments, the first position limiting block 1285 may include a first photoelectric wafer 1285-1 and a first photoelectric sensor 1285-2. The first photoelectric wafer 1285-1 may be fixedly connected with one end of the first slice plate holder 1225-1 (e.g., fixedly connected with the second end of the first slice plate holder 1225-1), and the first photoelectric sensor 1285-2 may be mounted on the support 1220. Correspondingly, the second position limiting block 1290 may include a second photoelectric wafer 1290-1 and a second photoelectric sensor 1290-2. The second photoelectric wafer 1290-1 may be fixedly connected to one end of the second slice plate holder 1230-1 (e.g., fixedly connected with the first end of the second slice plate holder 1230-1), and the second photoelectric sensor 1290-2 may be mounted on the support 1220. In some embodiments, the first photoelectric sensor 1285-2 and the second photoelectric sensor 1290-2 may work with the first photoelectric wafer 1285-1 and the second photoelectric wafer 1290-1, respectively. The cooperation of a photoelectric sensor and the corresponding photoelectric wafer may allow the detection of the position of the slice plate unit 1210 connected to them, thereby detecting the size and the position of the opening.

In some embodiments, the first end of the first slice plate holder 1225-1 may be fixedly connected with the first screw nut base 1235-2 and the first slider 1265. The first slider 1265 and the first linear guide 1255 may be placed under the first screw nut base 1235-2. The second end of the first slice plate holder 1225-1 may be fixedly connected with the first photoelectric wafer 1285-1. The first photoelectric wafer 1285-1 may be placed under the second ball screw 1240-1. Correspondingly, the second end of the second slice plate holder 1230-1 may be fixedly connected with the second screw nut base 1240-2 and the second slider 1270. The second slider 1270 and the second linear guide 1260 may be placed under the second screw nut base 1240-2. The first end of the first slice plate holder 1225-1 may be fixedly connected with the first photoelectric wafer 1285-1. The second photoelectric wafer 1290-1 may be placed under the first screw ball 1235-1. By making use of the space between the two opposite ends (the first end and the second end) of the first slice plate holder 1225-1 and the second slice plate holder 1230-1, the structure shown in FIG. 12a may make the slice module 1205 more compact and the size of the scanning system 100 smaller.

In some embodiments, the slice module 1205 may further include a first driver (not shown in FIG. 12a) connected with the first actuator 1235 and a second driver (not shown in FIG. 12a) connected with the second actuator 1240. The first actuator 1235 and the second actuator 1240 may be connected with the first driver and the second driver (not shown in FIG. 12a), respectively. Therefore, the movement of a single slice plate may be controlled by controlling a single driver to improve the gearing accuracy. The size and position of the opening between the first slice plate 1225-2 and the second slice plate 1230-2 may be more conveniently controlled.

Figure 12B:
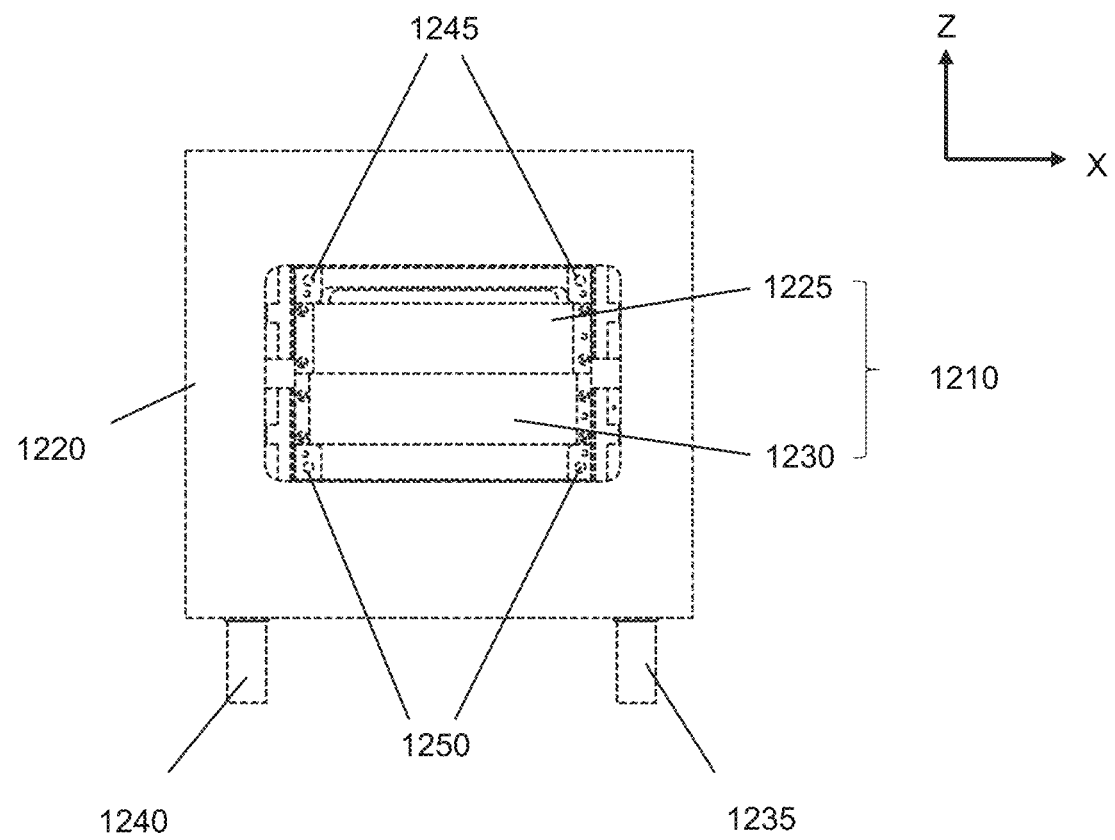
FIG. 12b is a bottom view of the exemplary slice module according to some embodiments of the present disclosure.

FIG. 12b is a bottom view of an exemplary slice module according to some embodiments of the present disclosure. As shown in FIG. 12b, the slice module 1205 may include the slice plate unit 1210, the actuator 1215, and the support 1220. Further, the slice plate unit 1210 may include the first slice plate component 1225 and the second slice plate component 1230. The actuator 1215 may include the first actuator 1235 corresponding to the first slice plate component 1225 and the second actuator 1240 corresponding to the second slice plate component 1230. The slice module 1205 may further include the first position block 1245 and the second position block 1250. In some embodiments, an adjustment gap may be preserved between the first position block 1245 and the first slice plate 1225-2, and an adjustment gap between the second position block 1250 and the second slice plate 1230-2, to allow an alignment of the first slice plate 1225-2 and the second slice plate relative to the detector 140 along the Z-axis direction during assembly.

Figure 13A:
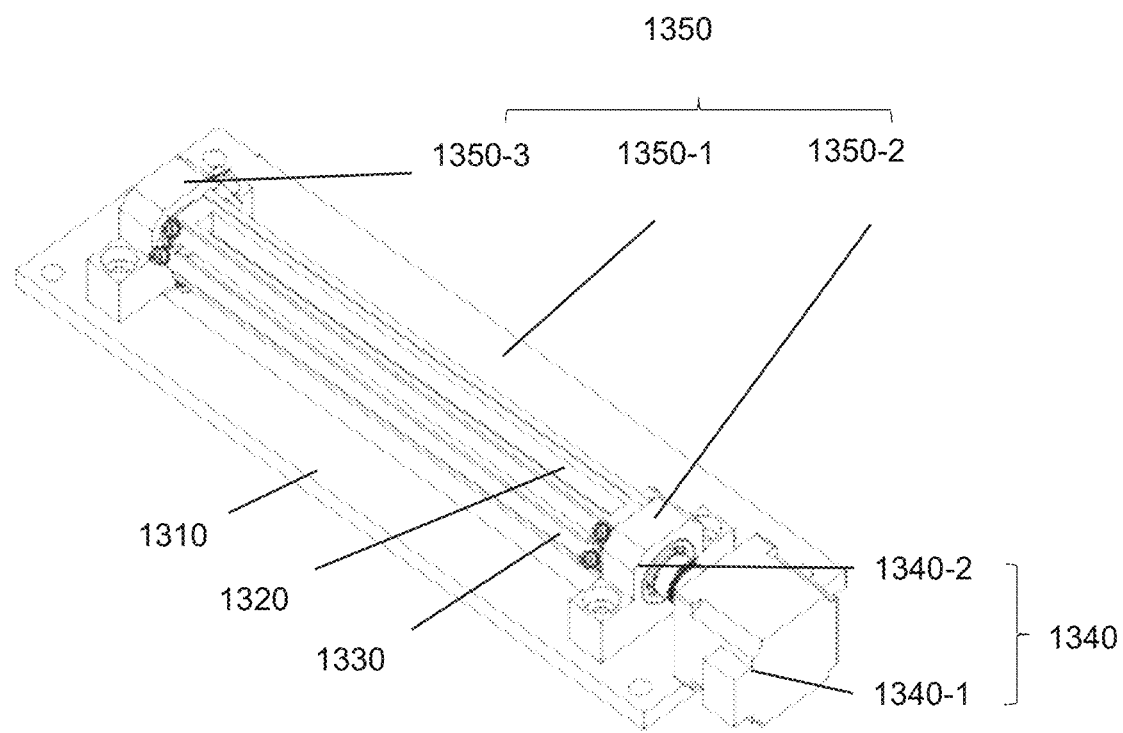
FIG. 13a is a schematic diagram of an exemplary slice module according to some embodiments of the present disclosure.

FIG. 13*a* is a schematic diagram of an exemplary slice module according to some embodiments of the present disclosure. The slice module 1310 may correspond to the slice module 800 shown in FIG. 8. As shown in FIG. 13*a*, the slice module 1310 may include a rotatable drum 1320, one or more slice plates 1330 with openings, an actuator 1340, and a support 1350. The actuator 1340 may include a motor 1340-1 and a coupling 1340-2. The motor 1340-1 may be mounted on the support 1350. The motor 1340-1 may be connected with one end of the drum 1320 through the coupling 1340-2. The drum 1320 may rotate around the axis of the motor 1340-1. When the slice control module 320 receives an angle adjustment instruction, the slice control module 320 may control the motor 1340-1 to drive the drum 1320 to rotate to a specified angle. By changing the rotation angle of the drum 1320, a specific slice plate 1330 and a corresponding through hole 1360 may be selected, thereby adjusting or modifying the fan-beam width of the rays and the position of the fan-beam of the rays.

The support 1350 may include a base plate 1350-1, a front bearing bracket 1350-2, and a back bearing bracket 1350-3. The front bearing bracket 1350-2 and the back bearing bracket 1350-3 may be mounted on the base plate 1350-1. Further, two ends of the drum 1320 may be connected with the front bearing bracket 1350-2 and the back bearing bracket 1350-3, respectively. The connection and the support of the base plate 1350-1, the coupling 1340-2, the front bearing bracket 1350-2, and the back bearing bracket 1350-3 may make the rotation of the drum 1320 more stable, thereby improving the operation precision of the scanning system 100.

Figure 13B:
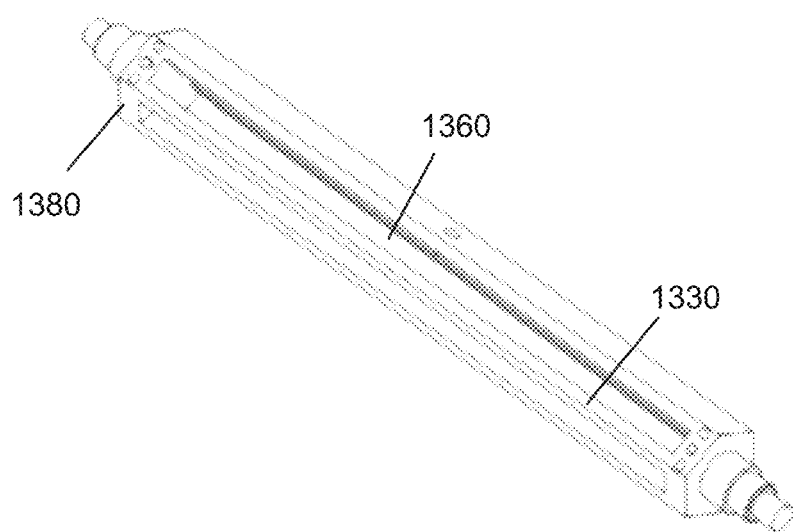
FIG. 13b is a schematic diagram of an exemplary drum according to some embodiments of the present disclosure.

FIG. 13*b* is a schematic diagram of an exemplary drum according to some embodiments of the present disclosure. The drum 1320 may rotate around an axis thereof. In some embodiments, the drum 1320 may have a cylindrical structure. The cylindrical structure may have one or more through holes 1360. Further, the one or more slice plate 1330 may be mounted on the lateral surface of the cylindrical structure. In some embodiments, the size(s) and the position(s) of the one or more through holes 1360 may correspond to the size(s) and the position(s) of the opening(s) of the one or more slice plates 1330. In some embodiments, the size(s) of the opening(s) of the one or more slice plates 1330 may be different from the size(s) of the one or more through holes 1360. For example, the size(s) of the opening(s) of the one or more slice plates 1330 may be smaller than the size(s) of the one or more through holes 1360. Further, the through hole 1360 may extend in a direction perpendicular to the plane formed by the slice plate 1330. In some embodiments, the position(s) of the one or more through holes 1360 may not overlap with each other. Therefore, the position(s) of one or more slice plates 1330 that correspond to the one of more through holes 1360 may also not overlap. In some embodiments, the drum 1320 may be a polygonal cylinder. The lateral surface of the drum 1320 may include an even number of faces 1380 forming pairs each of which are opposite to each other. Further, the count of the through holes 1360, the count of slice plates 1330, and the count of the face pairs may be the same. A slice plate 1330 may be mounted on either face of each face pair. A through hole 1360 may connect two faces 1380 of the corresponding face pair. In some embodiments, the drum 1320 may be of another shape (e.g., cylinder).

Figure 13C:
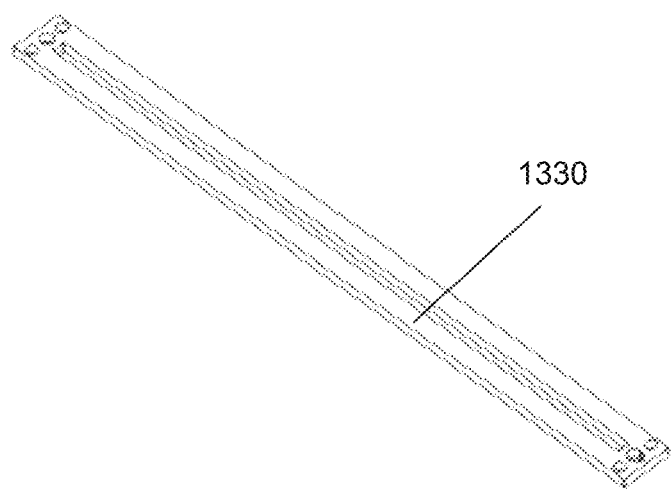
FIG. 13c is a schematic diagram of an exemplary slice plate according to some embodiments of the present disclosure.

FIG. 13*c* is a schematic diagram of an exemplary slice plate according to some embodiments of the present disclosure. The slice plate 1330 may be a plate with an opening. The opening may have the shape of a rectangle, a strip, an oval, etc. In some embodiments, the slice plate 1330 may be detachably connected with the drum 1320 so that the slice plate 1330 may be easily replaced or repaired. In some embodiments, the slice plate 1330 and the drum 1320 may be an integral structure. In some embodiments, the sizes and shapes of the openings of the one or more slice plates 1330 may be partially or totally different to satisfy different adjustment needs of the size and the position of the fan-beam of the rays. In some embodiments, the slice module 1310 may include the drum 1320 but not the slice plates 1330. The surface or the whole body of the drum 1320 may realize the function of the slice plates 1330 described elsewhere in the present disclosure. Rays 1370 may enter from one side of the drum 1320, pass through the through holes 1360, and exit from the opposite side of the drum 1320.

Figure 13D:
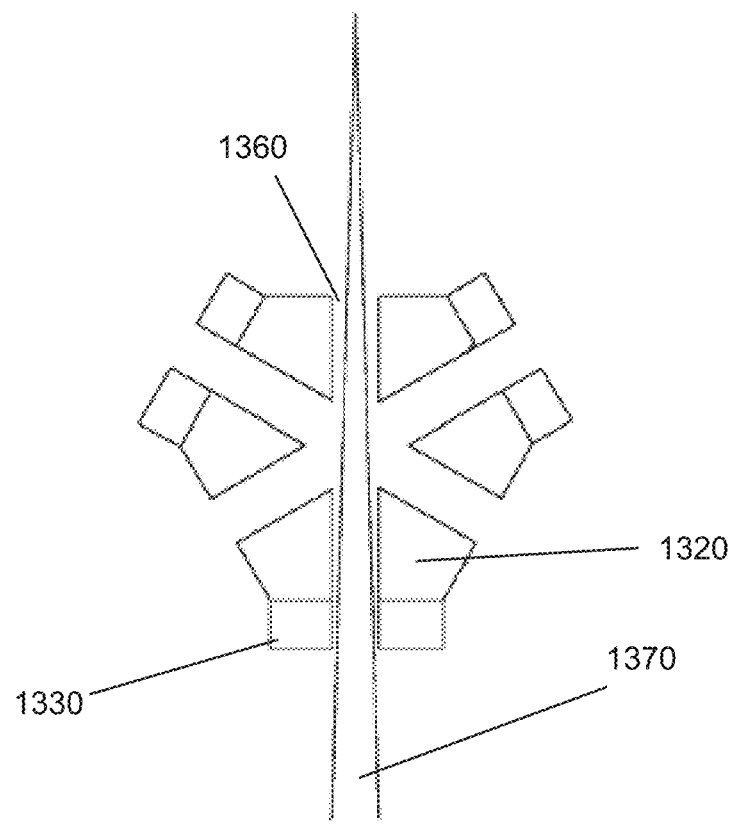
FIG. 13d is a schematic diagram of exemplary slice plates under radiation with traversing rays according to some embodiments of the present disclosure.

FIG. 13*d* is a schematic diagram of exemplary slice plates with traversing rays according to some embodiments of the present disclosure. In some embodiments, rays entering from slice plate 1330 located on one side of the cylindrical structure may exit from the opposite side of the cylindrical structure after passing through the corresponding through hole 1360. Further, the size and the position of the fan-beam of the rays may be adjusted by changing the structures of the slice plate 1330 and the through hole 1360. In some embodiments, the rays may enter from any one of the slice plates 1330 by rotating the drum 1320 to adjust the size and the position of the fan-beam of the rays.

In some embodiments, the slice plates 1330 may be mounted on every other lateral face of a polygonal cylinder. That is, each two slice plates 1330 may be separated by a face 1380 that does not include a slice plate 1330. The structure may simplify the arrangement of the slice plates 1330 and the through holes 1360. The structure may also improve the precision of the adjustment of the slice plates 1330 during the rotation of the drum 1320. In some embodiments, the count of the faces may be six, and the count of the face pairs, the count of the slice plates 1330, and the count of the through holes may be three.

We claim:

1. A collimator comprising:
   a support and protection module having a box structure, the box structure having a top opening and a side opening;
   a filter module configured to be placed into and pulled from the box structure from the side opening of the box structure, and
   a slice module configured to be mounted on the box structure from the top opening and close the top opening, wherein the filter module and the slice module are detachably connected with the support and protection module.

2. The collimator of claim 1, wherein the slice module comprises:
   two slice plates, an opening being formed between the two slice plates;
   an actuator configured to control movement of the two slice plates, the size of the opening being adjustable by moving the two slice plates; and
   a support on which the two slice plates and the actuator after being assembled are placed.

3. The collimator of claim 2, wherein the support includes a plate with a hollow part, and the hollow part of the support is positioned corresponding to the opening.

4. The collimator of claim 3, wherein the actuator is placed in the hollow part of the support.

5. The collimator of claim 1, wherein the slice module comprises:
a drum that is capable of rotating around an axis of the drum, a lateral surface of the drum having a through hole to allow rays to pass through.

6. The collimator of claim 5, the slice module further comprising a slice plate with an opening, the slice plate being placed on an external side of the drum, wherein the rays pass through the opening and the through hole and exit from a side of the drum opposite to the opening.

7. The collimator of claim 6, wherein the opening has a shape of a stripe, a rectangle, or an oval.

8. The collimator of claim 6, wherein the slice plate is a flat plate and the through hole extends in a direction perpendicular to a plane formed by the slice plate.

9. The collimator of claim 5, wherein the drum has multiple through holes, and positions of the multiple through holes do not overlap with each other.

10. The collimator of claim 9, wherein
the slice module comprises multiple slice plates,
the drum is a polygonal cylinder, a lateral surface of the drum comprises multiple faces forming pairs each of which are opposite to each other,
two opposite faces of the multiple faces form a face pair,
a count of the through holes, a count of slice plates, and a count of the face pairs are the same,
each slice plate of the multiple slice plates is mounted on one face of each face pair, and
each through hole connects two faces of each face pair.

11. The collimator of claim 1, wherein the filter module comprises:
a filter replacing unit, the filter replacing unit comprising a filter holder, a filter mounting plate, and one or more first filters; and
a filter floating base, the filter floating base comprising an optical guide shaft, a linear bearing, a base, and one or more second filters.

12. The collimator of claim 11, wherein the one or more first filters are arranged side by side along a direction in which the filter module is placed into and pulled from the box structure.

13. The collimator of claim 11, wherein the linear bearing and the one or more second filters are placed on the base, the optical guide shaft is located in the linear bearing, and the optical guide shaft is capable of rotating and driving the base to move along an axial direction of the optical guide shaft.

14. The collimator of claim 11, wherein
a count of the one or more first filters is the same as a count of the one or more second filters, and
the one or more first filters and the one or more second filters are of a same type, and are arranged in one-to-one correspondence.

15. The collimator of claim 11, wherein the one or more first filters and the one or more second filters are butterfly filters or plate filters.

16. The collimator of claim 11, wherein the one or more first filters and the one or more second filters are arranged along the axial direction of the optical guide shaft.

17. The collimator of claim 11, wherein the one or more first filters are mounted on the filter mounting plate via the filter holder.

18. The collimator of claim 11, wherein the filter replacing unit is detachably mounted on the filter floating base.

19. The collimator of claim 11, wherein the filter floating base is configured to be placed into and pulled from the box structure from the side opening of the box structure.

20. The collimator of claim 11, wherein the one or more first filters or the one or more second filters are configured with different parameters.

* * * * *